United States Patent
Harada

(10) Patent No.: US 11,402,621 B2
(45) Date of Patent: Aug. 2, 2022

(54) OBJECTIVE LENS FOR ENDOSCOPE AND ENDOSCOPE

(71) Applicant: FUJIFILM Corporation, Tokyo (JP)

(72) Inventor: Keisuke Harada, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 267 days.

(21) Appl. No.: 16/735,712

(22) Filed: Jan. 7, 2020

(65) Prior Publication Data
US 2020/0225459 A1 Jul. 16, 2020

(30) Foreign Application Priority Data

Jan. 16, 2019 (JP) .............................. JP2019-005417
Sep. 19, 2019 (JP) .............................. JP2019-170758

(51) Int. Cl.
| | |
|---|---|
| *G02B 23/24* | (2006.01) |
| *G02B 13/04* | (2006.01) |
| *G02B 9/60* | (2006.01) |
| *A61B 1/00* | (2006.01) |
| *G02B 13/00* | (2006.01) |

(52) U.S. Cl.
CPC ........ *G02B 23/243* (2013.01); *A61B 1/00096* (2013.01); *G02B 9/60* (2013.01); *G02B 13/006* (2013.01); *G02B 13/04* (2013.01)

(58) Field of Classification Search
CPC .. G02B 23/243; G02B 23/2438; G02B 13/04; G02B 9/60; G02B 13/006; G02B 13/0045; A61B 1/00096; A61B 1/00163
USPC .................................................. 359/659, 753
See application file for complete search history.

(56) References Cited

U.S. PATENT DOCUMENTS

| | | | |
|---|---|---|---|
| 6,038,085 A | * | 3/2000 | Nakazawa ............... G02B 9/12 359/753 |
| 9,606,337 B2 | | 3/2017 | Ikeda et al. |
| 9,696,526 B2 | | 7/2017 | Inoue |

(Continued)

FOREIGN PATENT DOCUMENTS

| | | | |
|---|---|---|---|
| JP | H1164727 | | 3/1999 |
| JP | 2015-94922 | * | 5/2015 |

(Continued)

OTHER PUBLICATIONS

"Office Action of Japan Counterpart Application" with English translation thereof, dated Feb. 1, 2022, p. 1-p. 6.

*Primary Examiner* — Jordan M Schwartz
(74) *Attorney, Agent, or Firm* — JCIPRNET

(57) ABSTRACT

An objective lens for an endoscope consists of a first lens group that consists of a negative lens, a second lens group that consists of a negative lens, a third lens group that consists of a cemented lens, an aperture stop, a fourth lens group that consists of a single lens having positive refractive power or a cemented lens having positive refractive power as a whole, and a fifth lens group that consists of a cemented lens including two lenses having refractive power having signs different from each other and cemented to each other; and the first lens group, the second lens group, the third lens group, the fourth lens group, and the fifth lens group are arranged in this order from an object side toward an image side. The objective lens for an endoscope satisfies a predetermined conditional expression related to the cemented lenses.

16 Claims, 18 Drawing Sheets

(56) References Cited

U.S. PATENT DOCUMENTS

| | | | | |
|---|---|---|---|---|
| 2011/0310496 A1* | 12/2011 | Kubota | ............... | G02B 9/64 |
| | | | | 359/794 |
| 2013/0057972 A1 | 3/2013 | Lee | | |
| 2017/0023778 A1* | 1/2017 | Inoue | ............... | G02B 9/62 |
| 2017/0242221 A1* | 8/2017 | Kunugise | ............ | G02B 7/04 |
| 2020/0081231 A1 | 3/2020 | Komiyama | | |

FOREIGN PATENT DOCUMENTS

| | | |
|---|---|---|
| JP | 2016012119 | 1/2016 |
| JP | 2017026802 | 2/2017 |
| JP | 6161520 | 7/2017 |
| WO | 2018110526 | 6/2018 |

\* cited by examiner

EXAMPLE 1

EXAMPLE 4

EXAMPLE 5

EXAMPLE 8

OBJECTIVE LENS FOR ENDOSCOPE AND ENDOSCOPE

CROSS-REFERENCE TO RELATED APPLICATIONS

The present application claims priority under 35 U.S.C. § 119 to Japanese Patent Application No. 2019-005417, filed on Jan. 16, 2019 and Japanese Patent Application No. 2019-170758, filed on Sep. 19, 2019, the contents of which are hereby expressly incorporated herein by reference in their entirety.

BACKGROUND OF THE INVENTION

1. Field of the Invention

The present disclosure relates to an objective lens for an endoscope and an endoscope.

2. Description of the Related Art

In the related art, endoscopes have been used for the observation, treatment, and the like for the inside of a patient's body in a medical field. JP6161520B and JP2017-026802A disclose lens systems that can be used as an objective lens for an endoscope. Each of these lens systems comprises a group having negative refractive power and a group having positive refractive power that are arranged in this order from an object side toward an image side.

SUMMARY OF THE INVENTION

In recent years, image processing has been performed on an image picked up by the endoscope to create an image in which surface structures or the like are emphasized and to emphasize and observe a lesion portion. In such an observation, a laser source having a short wavelength near, for example, a wavelength of 400 nm (nanometer) is used as a light source in addition to a white light source. In this case, there is a demand for an objective lens for an endoscope of which a chromatic aberration is corrected well over the entire range to a visible range from a short wavelength range. In endoscopic observation accompanied by surgical treatment, a treatment range is required to be specified and the distortion of an image is required to be reduced for precise treatment. For this purpose, there is a demand for an objective lens for an endoscope of which distortion is corrected well. From the above description, it is desired that both a chromatic aberration and distortion are corrected well in a balanced manner in an objective lens for an endoscope.

However, it cannot be said that both a chromatic aberration and distortion of the lens system disclosed in JP6161520B are sufficiently corrected. There is room for improvement of the lens system disclosed in JP2017-026802A in terms of the balance between the correction of distortion and the correction of a lateral chromatic aberration.

The disclosure has been made in consideration of the above-mentioned circumstances, an object of the disclosure is to provide an objective lens for an endoscope of which both a chromatic aberration and distortion are corrected well and which has high optical performance, and an endoscope including the objective lens for an endoscope.

An objective lens for an endoscope according to an aspect of the disclosure consists of a first lens group that consists of a negative lens, a second lens group that consists of a negative lens, a third lens group that consists of a cemented lens formed by cementing two lenses, an aperture stop, a fourth lens group that consists of a single lens having positive refractive power or a cemented lens formed by cementing two lenses and having positive refractive power as a whole, and a fifth lens group that consists of a cemented lens formed by cementing two lenses having refractive power having signs different from each other; and the first lens group, the second lens group, the third lens group, the fourth lens group, and the fifth lens group are arranged in this order from an object side toward an image side. In a case where a total number of the cemented lenses is denoted by k, a natural number of 1 to k is denoted by i, an Abbe's number of a lens, which forms an i-th cemented lens from the object side and is close to the object side, with respect to a d line is denoted by vai, an Abbe's number of a lens, which forms the i-th cemented lens from the object side and is close to the image side, with respect to a d line is denoted by vbi, a distance on an optical axis between the aperture stop and a cemented surface of the i-th cemented lens from the object side is denoted by Dci, and a radius of curvature of the cemented surface of the i-th cemented lens from the object side is denoted by Rci, the objective lens for an endoscope satisfies Conditional expression (1).

$$100 < \sum_{i=1}^{k} \left|(vai - vbi) \times \frac{Dci}{Rci}\right| \tag{1}$$

It is preferable that the objective lens for an endoscope according to the aspect satisfies Conditional expression (1-1).

$$110 < \sum_{i=1}^{k} \left|(vai - vbi) \times \frac{Dci}{Rci}\right| < 200 \tag{1-1}$$

In a case where a composite focal length of the first lens group and the second lens group is denoted by f12, a focal length of the third lens group is denoted by f3, a radius of curvature of a surface of the negative lens of the first lens group close to the image side is denoted by Rr1, a radius of curvature of a surface of the negative lens of the first lens group close to the object side is denoted by Rf1, a radius of curvature of a surface of the negative lens of the second lens group close to the image side is denoted by Rr2, and a radius of curvature of a surface of the negative lens of the second lens group close to the object side is denoted by Rf2, it is preferable that the objective lens for an endoscope according to the aspect satisfies Conditional expression (2) and it is more preferable that the objective lens for an endoscope according to the aspect satisfies Conditional expression (2-1).

$$-3 < \frac{f12}{f3} \times \frac{Rr1 + Rf1}{Rr1 - Rf1} \times \frac{Rr2 + Rf2}{Rr2 - Rf2} < -1 \tag{2}$$

$$-1.8 < \frac{f12}{f3} \times \frac{Rr1 + Rf1}{Rr1 - Rf1} \times \frac{Rr2 + Rf2}{Rr2 - Rf2} < -1 \tag{2-1}$$

In a case where a radius of curvature of a surface of the third lens group closest to the image side is denoted by Rr3 and a focal length of the objective lens for an endoscope is denoted by f, it is preferable that the objective lens for an endoscope according to the aspect satisfies Conditional expression (3) and it is more preferable that the objective lens for an endoscope according to the aspect satisfies Conditional expression (3-1).

$$-20 < Rr3/f < -0.5 \quad (3)$$

$$-12 < Rr3/f < -1 \quad (3\text{-}1)$$

In a case where a radius of curvature of a surface of the fourth lens group closest to the image side is denoted by Rr4 and a focal length of the objective lens for an endoscope is denoted by f, it is preferable that the objective lens for an endoscope according to the aspect satisfies Conditional expression (4) and it is more preferable that the objective lens for an endoscope according to the aspect satisfies Conditional expression (4-1).

$$-2.5 < Rr4/f < -1 \quad (4)$$

$$-2.2 < Rr4/f < -1.2 \quad (4\text{-}1)$$

In a case where a radius of curvature of a surface of the fifth lens group closest to the image side is denoted by Rr5 and a radius of curvature of a surface of the fifth lens group closest to the object side is denoted by Rf5, it is preferable that the objective lens for an endoscope according to the aspect satisfies Conditional expression (5) and it is more preferable that the objective lens for an endoscope according to the aspect satisfies Conditional expression (5-1).

$$-0.5 < (Rr5+Rf5)/(Rr5-Rf5) < 1 \quad (5)$$

$$-0.25 < (Rr5+Rf5)/(Rr5-Rf5) < 0.7 \quad (5\text{-}1)$$

In a case where a distance on the optical axis between the aperture stop and a lens surface closest to the object side is denoted by Df and a distance on the optical axis between the aperture stop and a lens surface closest to the image side is denoted by Dr, it is preferable that the objective lens for an endoscope according to the aspect satisfies Conditional expression (6) and it is more preferable that the objective lens for an endoscope according to the aspect satisfies Conditional expression (6-1).

$$0.5 < Df/Dr < 1.5 \quad (6)$$

$$0.8 < Df/Dr < 1.2 \quad (6\text{-}1)$$

In a case where a composite focal length of the first lens group, the second lens group, and the third lens group is denoted by f123 and a composite focal length of the fourth lens group and the fifth lens group is denoted by f45, it is preferable that the objective lens for an endoscope according to the aspect satisfies Conditional expression (7) and it is more preferable that the objective lens for an endoscope according to the aspect satisfies Conditional expression (7-1).

$$1.5 < |f123/f45| < 10 \quad (7)$$

$$1.8 < |f123/f45| < 8 \quad (7\text{-}1)$$

An endoscope according to another aspect of the disclosure comprises the objective lens for an endoscope according to the aspect of the disclosure.

"Consisting of" and "consist of" in this specification may intend to include a lens substantially not having refractive power; optical elements other than a lens, such as a stop, a filter, and a cover glass; a lens flange; a lens barrel; an image pickup element; and the like other than described components.

"~ group having positive refractive power" in this specification means that a group has positive refractive power as a whole. Likewise, "~ group having negative refractive power" means that a group has negative refractive power as a whole. "Lens having positive refractive power" and "positive lens" are synonymous with each other. "Lens having negative refractive power" and "negative lens" are synonymous with each other.

"Single lens" means one lens that is not cemented. A compound aspherical lens (a lens of which a spherical lens and an aspherical film formed on the spherical lens are integrated and which functions as one aspherical lens as a whole) is treated as one lens without being regarded as a cemented lens. The sign of refractive power, the radius of curvature of the lens surface, and the shape of the lens surface of a lens including an aspheric surface are considered in a paraxial region unless otherwise specified. With regard to the sign of a radius of curvature, the sign of the radius of curvature of a surface having a convex shape toward an object side is positive and the sign of the radius of curvature of a surface having a convex shape toward an image side is negative.

In this specification, a "focal length" used in Conditional expressions is a paraxial focal length. Values in Conditional expressions are values that are obtained in a case where a d line is used as a reference. "d line", "C line", and "F line" described in this specification are emission lines, and the wavelength of a d line is 587.56 nm (nanometer), the wavelength of the C line is 656.27 nm (nanometer), and the wavelength of the F line is 486.13 nm (nanometer). In this specification, "in this order from the object side" about an arrangement order is synonymous with "in this order from the object side toward the image side".

According to the disclosure, it is possible to provide an objective lens for an endoscope of which both a chromatic aberration and distortion are corrected well and which has high optical performance, and an endoscope including the objective lens for an endoscope.

DESCRIPTION OF THE PREFERRED EMBODIMENTS

Figure 1:
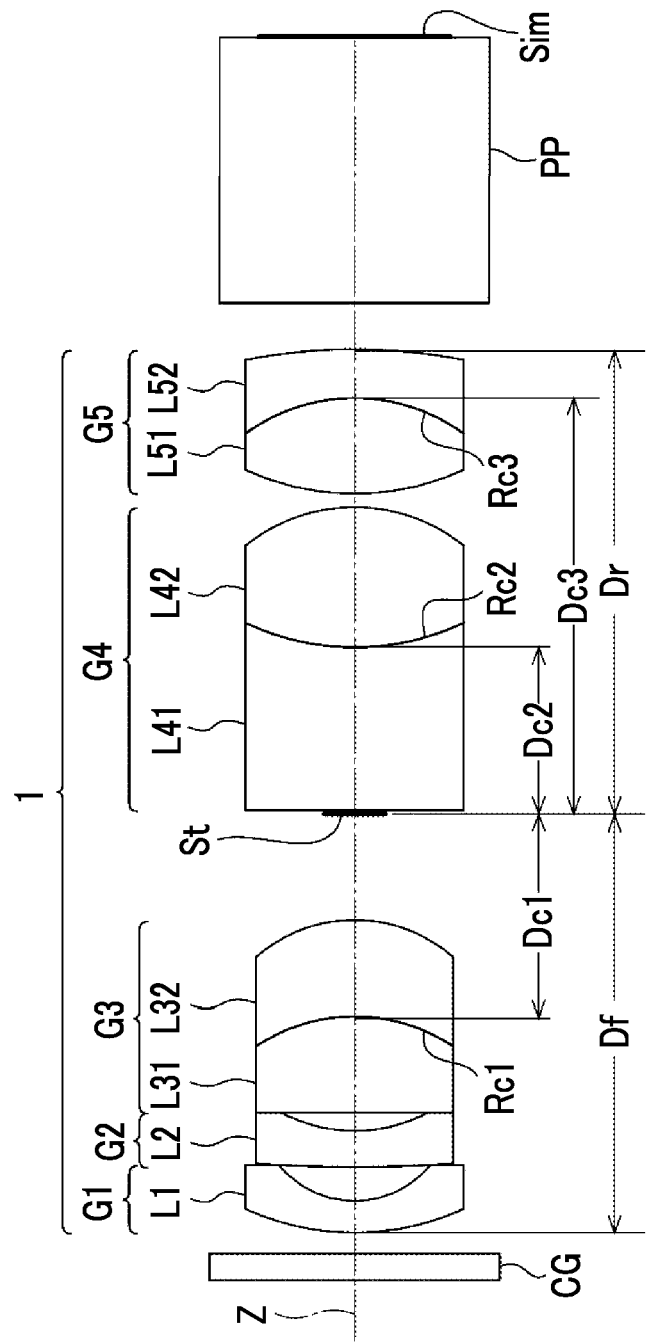
FIG. 1 is a cross-sectional view showing the configuration of an objective lens for an endoscope according to an embodiment of the disclosure.

Embodiments of the disclosure will be described in detail below with reference to the drawings. FIG. 1 is a cross-sectional view showing the configuration of an objective lens 1 for an endoscope according to an embodiment of the disclosure. An example shown in FIG. 1 corresponds to Example 1 to be described later. In FIG. 1, a left side is an object side and a right side is an image side.

FIG. 1 shows an example where a cover glass CG is disposed on the object side of the objective lens 1 for an endoscope and an optical member PP is disposed on the image side of the objective lens 1 for an endoscope in consideration of a use situation. The optical member PP is a member that is assumed as various filters and/or a prism and the like. Various filters include, for example, a low-pass filter, an infrared cut filter, a filter that cuts a specific wavelength range, and the like. Each of the cover glass CG and the optical member PP is a member of which an incident surface and an emitting surface are parallel to each other and which does not have refractive power, and is not a lens. At least one of the cover glass CG or the optical member PP may be omitted in the disclosure. Further, an example where an image plane Sim is positioned on the surface of the optical member PP close to the image side is shown in FIG. 1, but the position of the image plane Sim is not limited to this position in the disclosure. The image plane Sim shown in FIG. 1 shows not a size but a position on an optical axis.

The objective lens 1 for an endoscope of the disclosure consists of a first lens group G1, a second lens group G2, a third lens group G3, an aperture stop St, a fourth lens group G4, and a fifth lens group G5 that are arranged along an optical axis Z in this order from the object side toward the image side. The first lens group G1 consists of one negative lens. The second lens group G2 consists of one negative lens. The third lens group G3 consists of a cemented lens that is composed of two lenses cemented to each other. The fourth lens group G4 consists of one single lens that has positive refractive power or a cemented lens that is composed of two lenses cemented to each other and has positive refractive power as a whole. That is, the fourth lens group G4 consists of one lens component having positive refractive power. The "lens component" is a lens of which only two surfaces, that is, a surface close to the object side and a surface close to the image side are air contact surfaces positioned on an optical axis, and one lens component means one single lens or one cemented lens. The fifth lens group G5 consists of a cemented lens composed of two lenses that have refractive power having signs different from each other and are cemented to each other. The cemented lens, which consists of two lenses having refractive power having signs different from each other, may be a cemented lens that consists of a positive lens and a negative lens arranged in this order from the object side and cemented to each other, and may be a cemented lens that consists of a negative lens and a positive lens arranged in this order from the object side and cemented to each other.

Since the first lens group G1 and the second lens group G2 are formed as described above, two negative lenses are successively arranged from a position closest to the object side. Accordingly, it is advantageous in terms of suppressing distortion while maintaining a wide angle of view.

Since the third lens group G3 is composed of two lenses cemented to each other, it is advantageous in terms of a reduction in size. In a case where the third lens group G3 consists of two lenses having refractive power having signs different from each other, it is advantageous in terms of the correction of a lateral chromatic aberration. In a case where the third lens group G3 consists of two positive lenses, it is advantageous in terms of the correction of distortion.

Since the aperture stop St is disposed substantially in the middle of a lens system as described above, a lens system having good symmetry with respect to the aperture stop St can be formed. As a result, it is advantageous in terms of the suppression of distortion. The aperture stop St shown in FIG. 1 shows not a shape but a position on the optical axis.

Since the fourth lens group G4 has the above-mentioned configuration in a lens system of which the first lens group G1 and the second lens group G2 have negative refractive power, the generation of astigmatism and field curvature can be suppressed. In a case where the fourth lens group G4 consists of one single lens, it is advantageous in terms of a reduction in size. In a case where the fourth lens group G4 consists of a cemented lens composed of two lenses that have refractive power having signs different from each other and are cemented to each other, it is advantageous in terms of the correction of a chromatic aberration.

The fifth lens group G5 is a lens group that is far from the aperture stop St and is closest to the image plane Sim. Since the fifth lens group G5 has the above-mentioned configuration, it is advantageous in terms of the correction of a lateral chromatic aberration.

For example, the objective lens 1 for an endoscope shown in FIG. 1 is adapted so that the first lens group G1 consists of one lens L1, the second lens group G2 consists of one lens L2, the third lens group G3 consists of two lenses L31 and L32 arranged in this order from the object side toward the image side, the fourth lens group G4 consists of two lenses L41 and L42 arranged in this order from the object side toward the image side, and the fifth lens group G5 consists of two lenses L51 and L52 arranged in this order from the object side toward the image side.

In a case where the total number of the cemented lenses included in the objective lens 1 for an endoscope is denoted by k; a natural number of 1 to k is denoted by i, the Abbe's number of a lens, which forms the i-th cemented lens from the object side and is close to the object side, with respect to a d line is denoted by vai, the Abbe's number of a lens, which forms the i-th cemented lens from the object side and is close to the image side, with respect to a d line is denoted by vbi, a distance on the optical axis between the aperture stop St and the cemented surface of the i-th cemented lens from the object side is denoted by Dci, and the radius of curvature of the cemented surface of the i-th cemented lens from the object side is denoted by Rci, the objective lens 1 for an endoscope is adapted to satisfy Conditional expression (1). Since $\Sigma(vai-vbi) \times Dci/Rci$ is made to be larger than the lower limit of Conditional expression (1), it is easy to correct an axial chromatic aberration and a lateral chromatic aberration to be generated in the first lens group G1 and the second lens group G2. In addition, it is preferable that the objective lens 1 for an endoscope satisfies Conditional expression (1-1). Since $\Sigma(vai-vbi) \times Dci/Rci$ is made to be larger than the lower limit of Conditional expression (1-1), it is easier to correct an axial chromatic aberration and a lateral chromatic aberration to be generated in the first lens group G1 and the second lens group G2. Since $\Sigma(vai-vbi) \times Dci/Rci$ is made to be smaller than the upper limit of Conditional expression (1-1), it is advantageous in terms of a reduction in the size of the lens system in the direction of the optical axis.

$$100 < \sum_{i=1}^{k} \left| (vai - vbi) \times \frac{Dci}{Rci} \right| \tag{1}$$

$$110 < \sum_{i=1}^{k} \left| (vai - vbi) \times \frac{Dci}{Rci} \right| < 200 \tag{1-1}$$

In the example shown in FIG. 1, the total number of the cemented lenses included in the objective lens 1 for an endoscope is 3. For example, in FIG. 1, distances on the optical axis between the aperture stop St and the cemented surfaces of the first, second, and third cemented lenses from the object side are denoted by Dc1, Dc2, and Dc3, respectively, and the radii of curvature of the cemented surfaces of the first, second, and third cemented lenses from the object side are denoted by Rc1, Rc2, and Rc3, respectively.

In a case where the composite focal length of the first lens group G1 and the second lens group G2 is denoted by f12, the focal length of the third lens group G3 is denoted by f3, the radius of curvature of the surface of the negative lens of the first lens group G1 close to the image side is denoted by Rr1, the radius of curvature of the surface of the negative lens of the first lens group G1 close to the object side is denoted by Rf1, the radius of curvature of the surface of the negative lens of the second lens group G2 close to the image side is denoted by Rr2, and the radius of curvature of the surface of the negative lens of the second lens group G2 close to the object side is denoted by Rf2, it is preferable that the objective lens 1 for an endoscope satisfies Conditional expression (2). (Rr1+Rf1)/(Rr1−Rf1) and (Rr2+Rf2)/(Rr2−Rf2) of Conditional expression (2) are terms related to the shape of the lens of the first lens group G1 and the shape of the lens of the second lens group G2, respectively. Since f12/f3×(Rr1+Rf1)/(Rr1−Rf1)×(Rr2+Rf2)/(Rr2−Rf2) is made to be larger than the lower limit of Conditional expression (2), it is easy to maintain a wide angle of view suitable for an objective optical system for an endoscope. Since f12/f3× (Rr1+Rf1)/(Rr1−Rf1)×(Rr2+Rf2)/(Rr2−Rf2) is made to be smaller than the upper limit of Conditional expression (2), it is easy to suitably control the refraction of an off-axis ray to suppress distortion. Better characteristics can be obtained in a case where the objective lens 1 for an endoscope is adapted to satisfy Conditional expression (2-1).

$$-3 < \frac{f12}{f3} \times \frac{Rr1 + Rf1}{Rr1 - Rf1} \times \frac{Rr2 + Rf2}{Rr2 - Rf2} < -1 \tag{2}$$

$$-1.8 < \frac{f12}{f3} \times \frac{Rr1 + Rf1}{Rr1 - Rf1} \times \frac{Rr2 + Rf2}{Rr2 - Rf2} < -1 \tag{2-1}$$

In a case where the radius of curvature of the surface of the third lens group G3 closest to the image side is denoted by Rr3 and the focal length of the objective lens 1 for an endoscope is denoted by f, it is preferable that the objective lens 1 for an endoscope satisfies Conditional expression (3). Since Rr3/f is made to be larger than the lower limit of Conditional expression (3), the positive refractive power of the surface of the third lens group G3 closest to the image side can be ensured. Accordingly, it is advantageous in terms of a reduction in size. Since Rr3/f is made to be smaller than the upper limit of Conditional expression (3), the positive refractive power of the surface of the third lens group G3 closest to the image side does not become excessive. Accordingly, it is possible to contribute to good correction of field curvature and astigmatism. Better characteristics can be obtained in a case where the objective lens 1 for an endoscope is adapted to satisfy Conditional expression (3-1).

$$-20 < Rr3/f < -0.5 \tag{3}$$

$$-12 < Rr3/f < -1 \tag{3-1}$$

In a case where the radius of curvature of the surface of the fourth lens group G4 closest to the image side is denoted by Rr4 and the focal length of the objective lens 1 for an endoscope is denoted by f, it is preferable that the objective lens 1 for an endoscope satisfies Conditional expression (4). Since Rr4/f is made to be larger than the lower limit of Conditional expression (4), the positive refractive power of the surface of the fourth lens group G4 closest to the image side can be ensured. Accordingly, it is advantageous in terms of a reduction in size. Since Rr4/f is made to be smaller than the upper limit of Conditional expression (4), the positive refractive power of the surface of the fourth lens group G4 closest to the image side does not become excessive. Accordingly, it is possible to contribute to good correction of distortion. Better characteristics can be obtained in a case where the objective lens 1 for an endoscope is adapted to satisfy Conditional expression (4-1).

$$-2.5 < Rr4/f < -1 \tag{4}$$

$$-2.2 < Rr4/f < -1.2 \tag{4-1}$$

In a case where the radius of curvature of the surface of the fifth lens group G5 closest to the image side is denoted by Rr5 and the radius of curvature of the surface of the fifth lens group G5 closest to the object side is denoted by Rf5, it is preferable that the objective lens 1 for an endoscope satisfies Conditional expression (5). Since (Rr5+Rf5)/(Rr5− Rf5) is made to be larger than the lower limit of Conditional expression (5), it is advantageous in terms of the correction of distortion. Since (Rr5+Rf5)/(Rr5−Rf5) is made to be smaller than the upper limit of Conditional expression (5), it is advantageous in terms of the correction of field curvature and it is advantageous in terms of a reduction in the incidence angle of a principal ray of off-axis luminous flux on the image plane Sim. Better characteristics can be obtained in a case where the objective lens 1 for an endoscope is adapted to satisfy Conditional expression (5-1).

$$-0.5<(Rr5+Rf5)/(Rr5-Rf5)<1 \quad (5)$$

$$-0.25<(Rr5+Rf5)/(Rr5-Rf5)<0.7 \quad (5\text{-}1)$$

In a case where a distance on the optical axis between the aperture stop St and a lens surface closest to the object side is denoted by Df and a distance on the optical axis between the aperture stop St and a lens surface closest to the image side is denoted by Dr, it is preferable that the objective lens 1 for an endoscope satisfies Conditional expression (6). For example, Df and Dr of the objective lens 1 for an endoscope are shown in FIG. 1. Since Df/Dr is made to be larger than the lower limit of Conditional expression (6), it is easy to suppress distortion while balancing the length of the lens system on the object side of the aperture stop St and the length of the lens system on the image side of the aperture stop St. Since Df/Dr is made to be smaller than the upper limit of Conditional expression (6), it is advantageous in terms of a reduction in the diameter of the lens closest to the object side. Better characteristics can be obtained in a case where the objective lens 1 for an endoscope is adapted to satisfy Conditional expression (6-1).

$$0.5<Df/Dr<1.5 \quad (6)$$

$$0.8<Df/Dr<1.2 \quad (6\text{-}1)$$

In a case where the composite focal length of the first lens group G1, the second lens group G2, and the third lens group G3 is denoted by f123 and the composite focal length of the fourth lens group G4 and the fifth lens group G5 is denoted by f45, it is preferable that the objective lens 1 for an endoscope satisfies Conditional expression (7). Conditional expression (7) is an expression related to a ratio of the composite refractive power of all the lens groups, which are positioned on the object side of the aperture stop St, to the composite refractive power of all the lens groups that are positioned on the image side of the aperture stop St. Since |f123/f45| is made to be larger than the lower limit of Conditional expression (7), it is advantageous in terms of correcting distortion well while maintaining a wide angle of view. Since |f123/f45| is made to be smaller than the upper limit of Conditional expression (7), it is easy to reduce the diameter of the lens closest to the object side while balancing the refractive power of the lenses positioned on the object side of the aperture stop St and the refractive power of the lenses positioned on the image side of the aperture stop St. Better characteristics can be obtained in a case where the objective lens 1 for an endoscope is adapted to satisfy Conditional expression (7-1).

$$1.5<|f123/f45|<10 \quad (7)$$

$$1.8<|f123/f45|<8 \quad (7\text{-}1)$$

Since not only the above-mentioned preferable configuration and/or possible configuration but also configuration related to Conditional expressions can be randomly combined, it is preferable that the above-mentioned preferable configuration, possible configuration, and configuration related to Conditional expressions are appropriately selectively employed according to specifications to be required.

According to the objective lens 1 for an endoscope of the embodiment of the disclosure, since both a chromatic aberration and distortion can be corrected well, high optical performance can be achieved.

Next, numerical examples of the objective lens for an endoscope according to the embodiment of the disclosure will be described. All data of Examples to be described below are data that are obtained in a case where the focal lengths of objective lenses for an endoscope are standardized to 1.

Example 1

Figure 2:
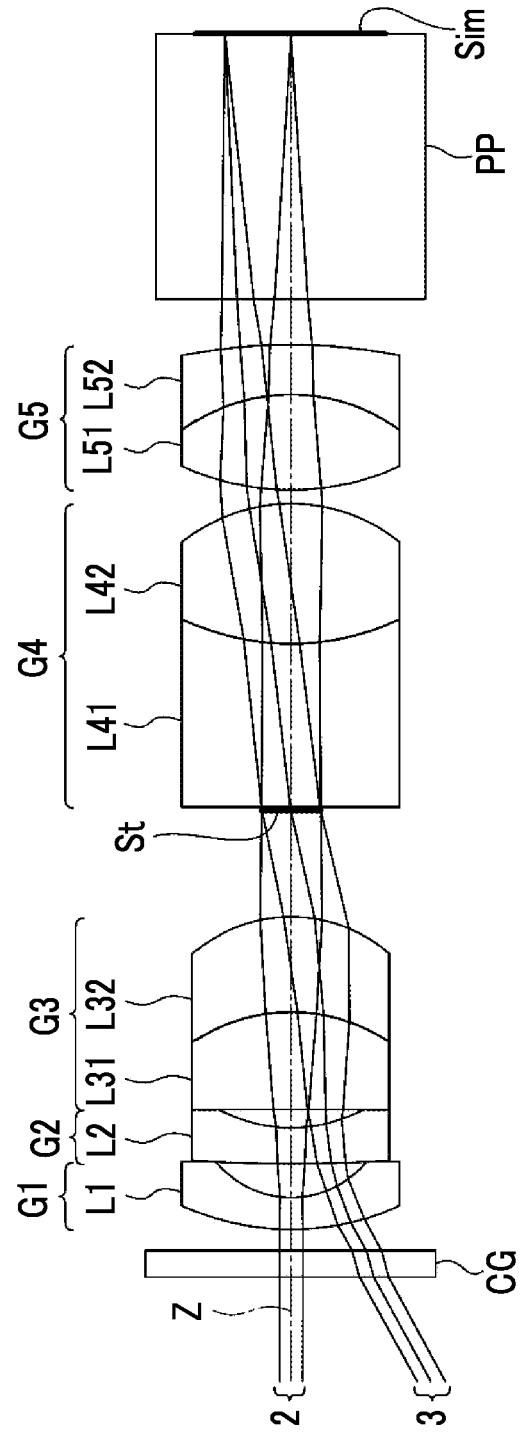
FIG. 2 is a cross-sectional view showing the configuration of an objective lens for an endoscope of Example 1 of the disclosure and luminous flux.

A cross-sectional view showing the configuration of an objective lens for an endoscope of Example 1 and luminous flux is shown in FIG. 2. On-axis luminous flux 2 and luminous flux 3, which corresponds to the maximum angle of view, are shown in FIG. 2 as luminous flux. Further, a cover glass CG and an optical member PP are also shown together in FIG. 2 as in FIG. 1 in consideration of a use situation. The objective lens for an endoscope of Example 1 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The aperture stop St shown in FIG. 2 shows not a shape but a position on an optical axis. The first lens group G1 consists of a negative lens L1. The second lens group G2 consists of a negative lens L2. The third lens group G3 consists of a cemented lens that includes a positive lens L31 and a positive lens L32 arranged in this order from the object side and cemented to each other. The fourth lens group G4 consists of a cemented lens that includes a negative lens L41 and a positive lens L42 arranged in this order from the object side and cemented to each other. The fifth lens group G5 consists of a cemented lens that includes a positive lens L51 and a negative lens L52 arranged in this order from the object side and cemented to each other.

The basic lens data of the objective lens for an endoscope of Example 1 are shown in Table 1, and the specifications thereof are shown in Table 2. In Table 1, surface numbers, which are obtained in a case where the surface closest to the object side is set as a first surface and the surface number is increased toward the image side from one by one, are written in the column of Sn, the radii of curvature of the respective surfaces are written in the column of R, and a surface interval on an optical axis between each surface and a surface, which is positioned on the image side of each surface so as to be adjacent to each surface, is written in the column of D. Further, the refractive indexes of the respective components with respect to a d line are written in the column of Nd, and the Abbe's numbers of the respective components with respect to a d line are written in the column of vd.

In Table 1, the sign of the radius of curvature of a surface having a convex shape toward the object side is positive and the sign of the radius of curvature of a surface having a convex shape toward the image side is negative. In Table 1, the cover glass CG, the aperture stop St, and the optical member PP are also shown and a surface number and the expression of (St) are written in the column of the surface number of a surface corresponding to the aperture stop St. A value of the lowest cell of the column of D in Table 1 is an interval between a surface closest to the image side and the image plane Sim in Table 1.

The value of the focal length f of the objective lens for an endoscope and the values of the back focus Bf, the F Number FNo., and the maximum total angle 1ω of view of the objective lens for an endoscope at an air conversion distance are shown in Table 2 with respect to a d line. (°) in the column of 2ω means that a unit is a degree. Numerical values, which are rounded off to a predetermined place, are written in Table 1 and Table 2.

TABLE 1

Example 1

| Sn | R | D | Nd | νd |
|---|---|---|---|---|
| 1 | ∞ | 0.2092 | 1.76800 | 71.70 |
| 2 | ∞ | 0.1673 | | |
| 3 | 2.1636 | 0.2510 | 2.00100 | 29.13 |
| 4 | 0.7973 | 0.2677 | | |
| 5 | 12.6576 | 0.2845 | 2.00100 | 29.13 |
| 6 | 1.2868 | 0.1422 | | |
| 7 | ∞ | 0.7613 | 2.00100 | 29.13 |
| 8 | −1.4574 | 0.7530 | 1.51680 | 64.13 |
| 9 | −1.2307 | 0.8366 | | |
| 10(St) | ∞ | 0.0293 | | |
| 11 | ∞ | 1.2884 | 1.88299 | 40.78 |
| 12 | 2.0950 | 1.1044 | 1.51633 | 64.05 |
| 13 | −1.4298 | 0.1088 | | |
| 14 | 2.1636 | 0.7530 | 1.51680 | 64.20 |
| 15 | −1.5210 | 0.3849 | 2.00069 | 25.46 |
| 16 | −4.5940 | 0.3598 | | |
| 17 | ∞ | 2.0916 | 1.55920 | 53.92 |
| 18 | ∞ | 0.0000 | | |

TABLE 2

Example 1

| f | 1.00 |
|---|---|
| Bf | 1.66 |
| FNo. | 4.99 |
| 2ω(°) | 80.2 |

Figure 10:
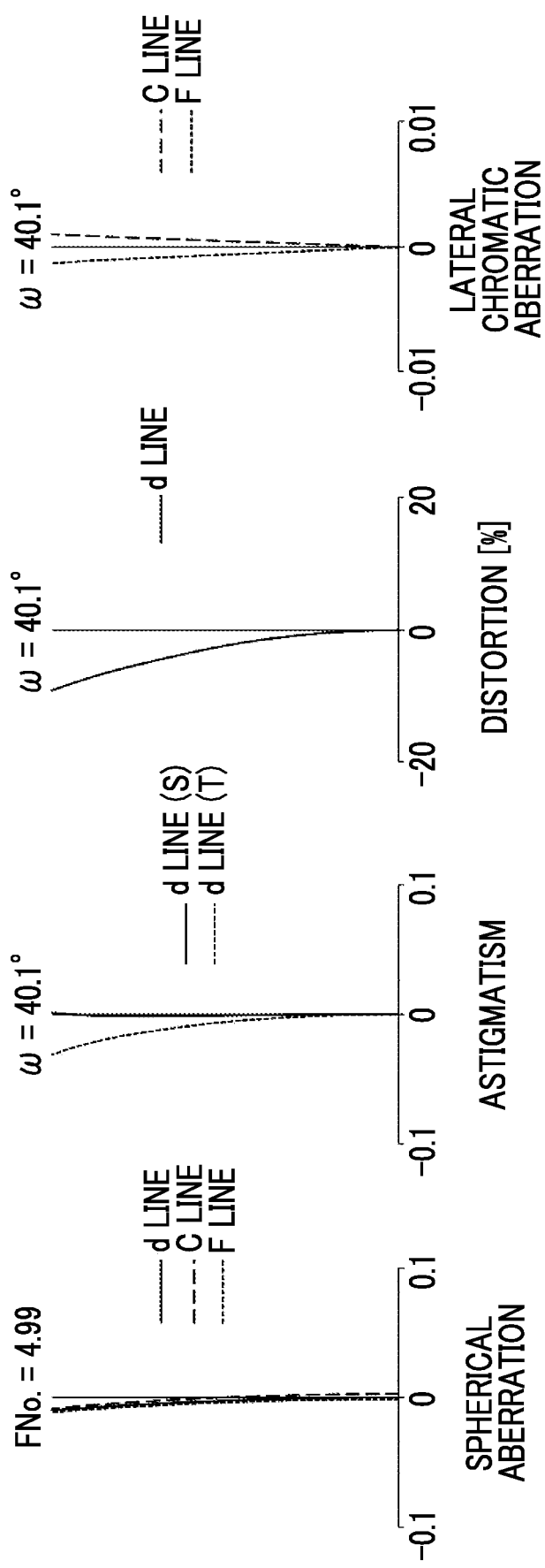
FIG. 10 is a diagram showing the respective aberrations of the objective lens for an endoscope of Example 1 of the disclosure.

A diagram showing the respective aberrations of the objective lens for an endoscope of Example 1 is shown in FIG. 10. A spherical aberration, astigmatism, distortion, and a lateral chromatic aberration are shown in FIG. 10 in this order from the left. In the diagram showing the spherical aberration, aberrations with respect to a d line, a C line, and an F line are shown by a solid line, a long-dashed line, and a short-dashed line, respectively. In the diagram showing the astigmatism, an aberration with respect to a d line in a sagittal direction is shown by a solid line and an aberration with respect to a d line in a tangential direction is shown by a short-dashed line. In the diagram showing the distortion, an aberration with respect to a d line is shown by a solid line. In the diagram showing the lateral chromatic aberration, aberrations with respect to a C line and an F line are shown by a long-dashed line and a short-dashed line, respectively. FNo. in the diagram showing the spherical aberration means an F number, and ω in the diagrams showing the other aberrations means the half angle of view. Data shown in Table 1 and FIG. 10 are data that are obtained in a case where a distance between an object and the surface of the cover glass CG close to the object side is set to 21.

Since the symbols, meanings, writing methods, illustrating methods for data about Example 1 are the same as those of other examples to be described below unless otherwise specified, the repeated description thereof will be omitted below.

Example 2

Figure 3:
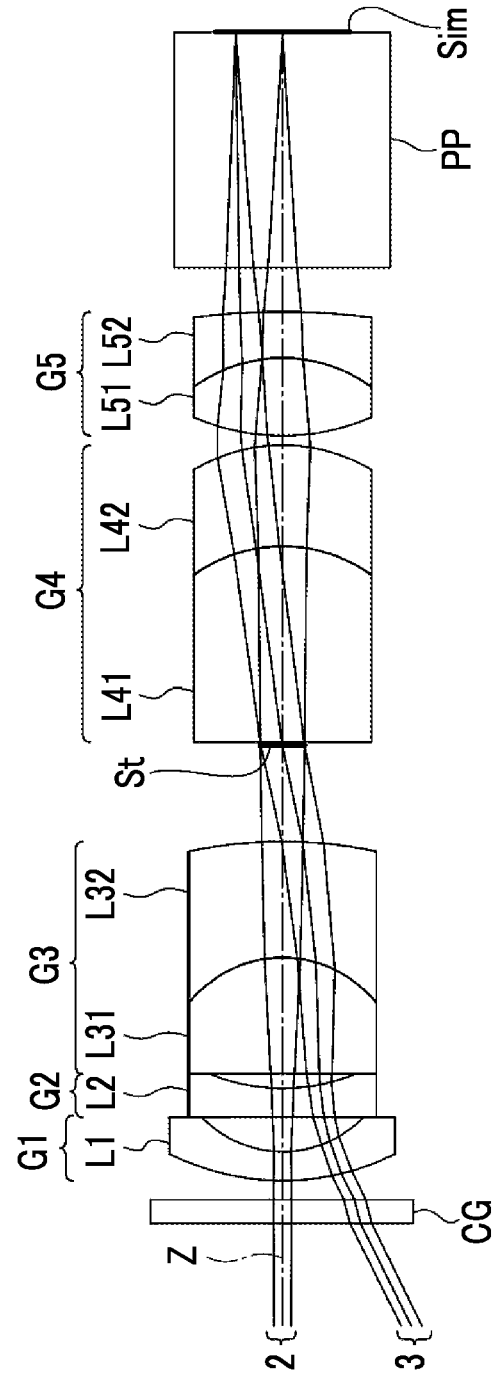
FIG. 3 is a cross-sectional view showing the configuration of an objective lens for an endoscope of Example 2 of the disclosure and luminous flux.

A cross-sectional view showing the configuration of an objective lens for an endoscope of Example 2 and luminous flux is shown in FIG. 3. The objective lens for an endoscope of Example 2 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a cemented lens that includes a positive lens L41 and a positive lens L42 arranged in this order from the object side and cemented to each other. The fifth lens group G5 consists of a cemented lens that includes a positive lens L51 and a negative lens L52 arranged in this order from the object side and cemented to each other.

Figure 11:
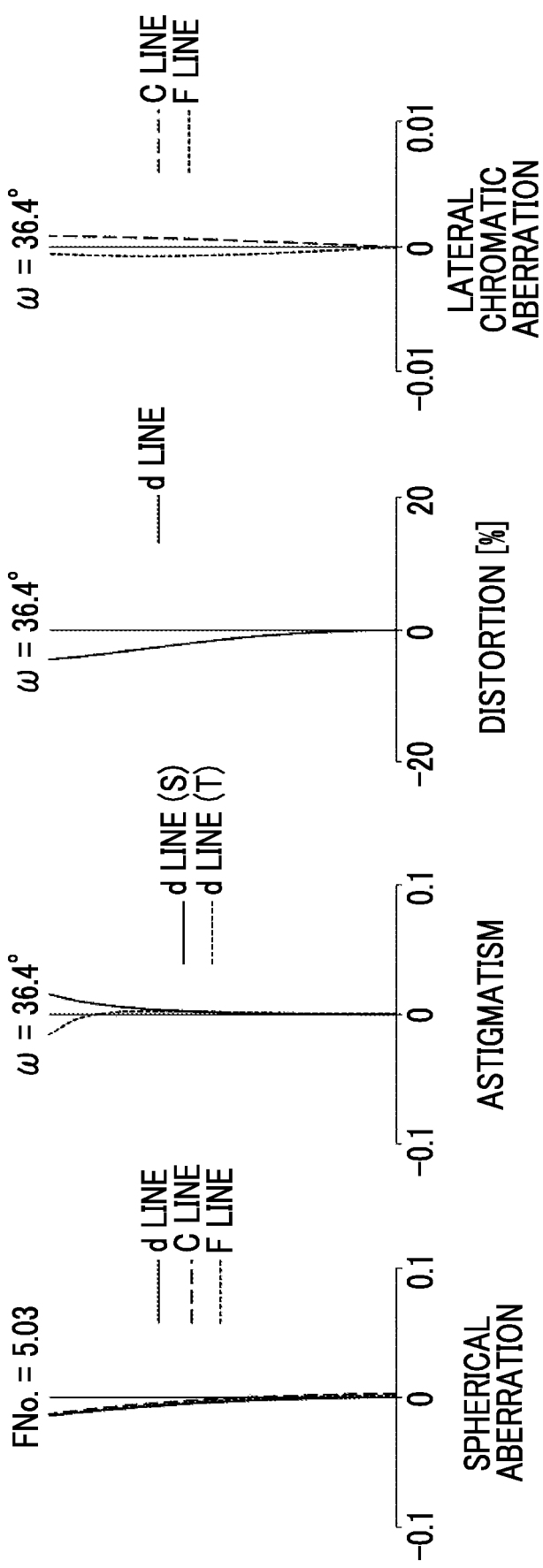
FIG. 11 is a diagram showing the respective aberrations of the objective lens for an endoscope of Example 2 of the disclosure.

The basic lens data of the objective lens for an endoscope of Example 2 are shown in Table 3, the specifications thereof are shown in Table 4, and a diagram showing the respective aberrations thereof is shown in FIG. 11. These data are data that are obtained in a case where a distance between an object and the surface of the cover glass CG close to the object side is set to 25.

TABLE 3

Example 2

| Sn | R | D | Nd | νd |
|---|---|---|---|---|
| 1 | ∞ | 0.2470 | 1.76800 | 71.70 |
| 2 | ∞ | 0.1976 | | |
| 3 | 2.7169 | 0.2964 | 2.05090 | 26.94 |
| 4 | 1.2053 | 0.3557 | | |
| 5 | −99.9066 | 0.2964 | 2.00100 | 29.13 |
| 6 | 2.0945 | 0.1482 | | |
| 7 | −99.9066 | 1.1954 | 2.00100 | 29.13 |
| 8 | −1.2883 | 1.1954 | 1.58144 | 40.75 |
| 9 | −4.8143 | 0.9880 | | |
| 10(St) | ∞ | 0.0346 | | |
| 11 | ∞ | 2.0056 | 1.51633 | 64.05 |
| 12 | −1.6410 | 1.0373 | 1.92286 | 20.88 |
| 13 | −1.8781 | 0.0988 | | |
| 14 | 2.4136 | 0.8003 | 1.51680 | 69.89 |
| 15 | −1.6410 | 0.4742 | 1.92286 | 20.88 |
| 16 | −7.7416 | 0.4564 | | |
| 17 | ∞ | 2.4205 | 1.55920 | 53.92 |
| 18 | ∞ | 0.0000 | | |

TABLE 4

Example 2

| f | 1.00 |
|---|---|
| Bf | 1.97 |
| FNo. | 5.03 |
| 2ω(°) | 72.8 |

Example 3

Figure 4:
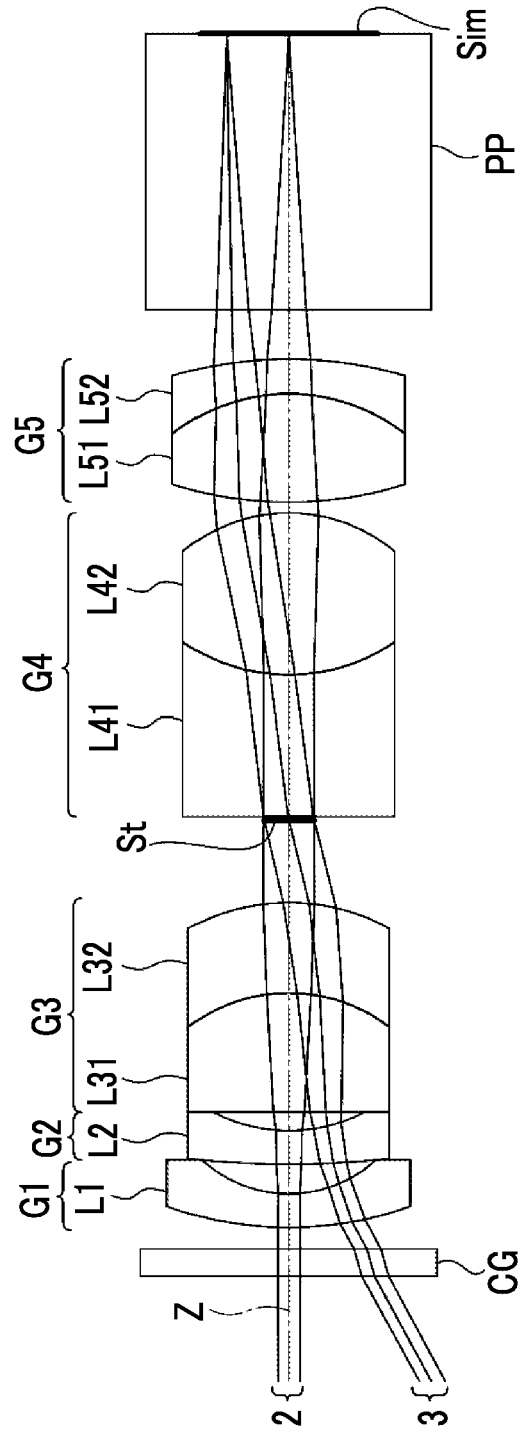
FIG. 4 is a cross-sectional view showing the configuration of an objective lens for an endoscope of Example 3 of the disclosure and luminous flux.

A cross-sectional view showing the configuration of an objective lens for an endoscope of Example 3 and luminous flux is shown in FIG. 4. The objective lens for an endoscope of Example 3 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a cemented lens that includes a negative lens L41 and a positive lens L42 arranged in this order from the object side and cemented to each other. The fifth lens group G5 consists of a cemented lens that includes a positive lens L51 and a negative lens L52 arranged in this order from the object side and cemented to each other.

Figure 12:
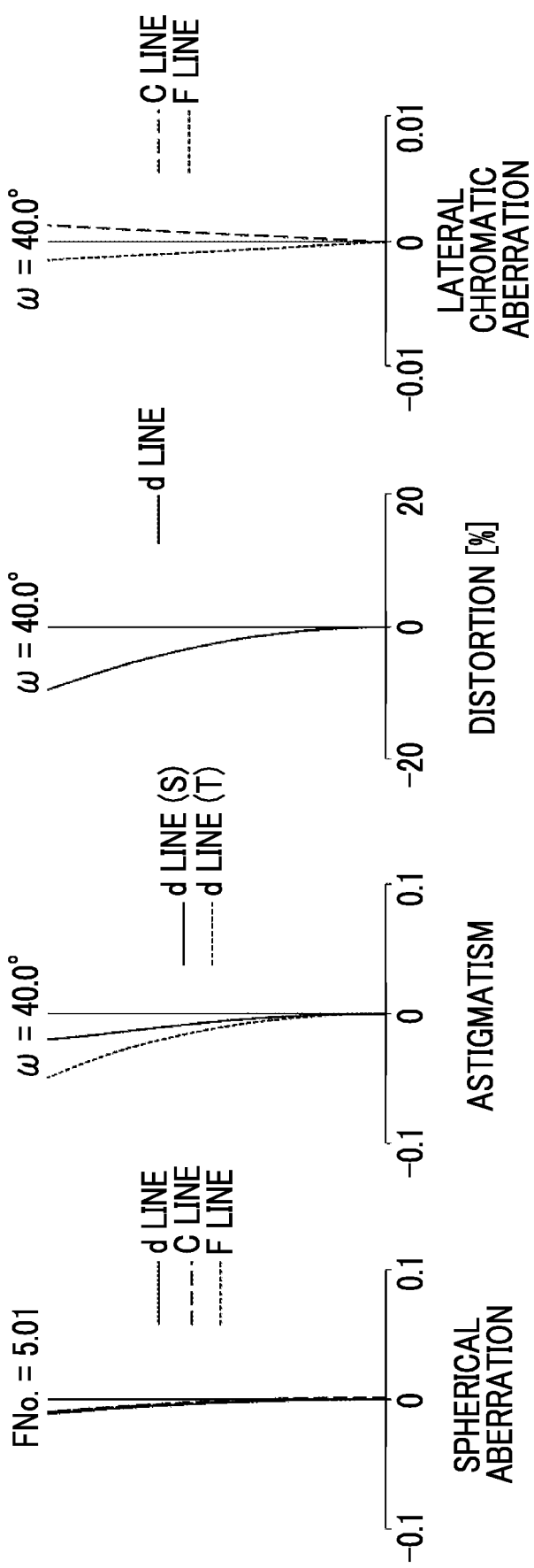
FIG. 12 is a diagram showing the respective aberrations of the objective lens for an endoscope of Example 3 of the disclosure.

The basic lens data of the objective lens for an endoscope of Example 3 are shown in Table 5, the specifications thereof are shown in Table 6, and a diagram showing the respective aberrations thereof is shown in FIG. 12. These data are data that are obtained in a case where a distance between an object and the surface of the cover glass CG close to the object side is set to 22.

TABLE 5

Example 3

| Sn | R | D | Nd | νd |
|---|---|---|---|---|
| 1 | ∞ | 0.2249 | 1.76800 | 71.70 |
| 2 | ∞ | 0.1799 | | |
| 3 | 3.1536 | 0.2788 | 2.00100 | 29.13 |
| 4 | 1.1244 | 0.2432 | | |
| 5 | 7.7077 | 0.2788 | 2.00100 | 29.13 |
| 6 | 1.4338 | 0.1529 | | |
| 7 | ∞ | 0.9894 | 2.00100 | 29.13 |
| 8 | −1.4338 | 0.7466 | 1.56384 | 60.67 |
| 9 | −1.8385 | 0.6836 | | |
| 10(St) | ∞ | 0.0315 | | |
| 11 | ∞ | 1.1693 | 1.88299 | 40.78 |
| 12 | 1.6353 | 1.3402 | 1.51860 | 69.89 |
| 13 | −1.4338 | 0.0899 | | |
| 14 | 3.3866 | 0.8995 | 1.62041 | 60.29 |
| 15 | −1.6353 | 0.2878 | 2.00069 | 25.46 |
| 16 | −3.6006 | 0.4028 | | |
| 17 | ∞ | 2.2937 | 1.55920 | 53.92 |
| 18 | ∞ | 0.0000 | | |

TABLE 6

Example 3

| f | 1.00 |
|---|---|
| Bf | 1.83 |
| FNo. | 5.01 |
| 2ω(°) | 80.0 |

Example 4

Figure 5:
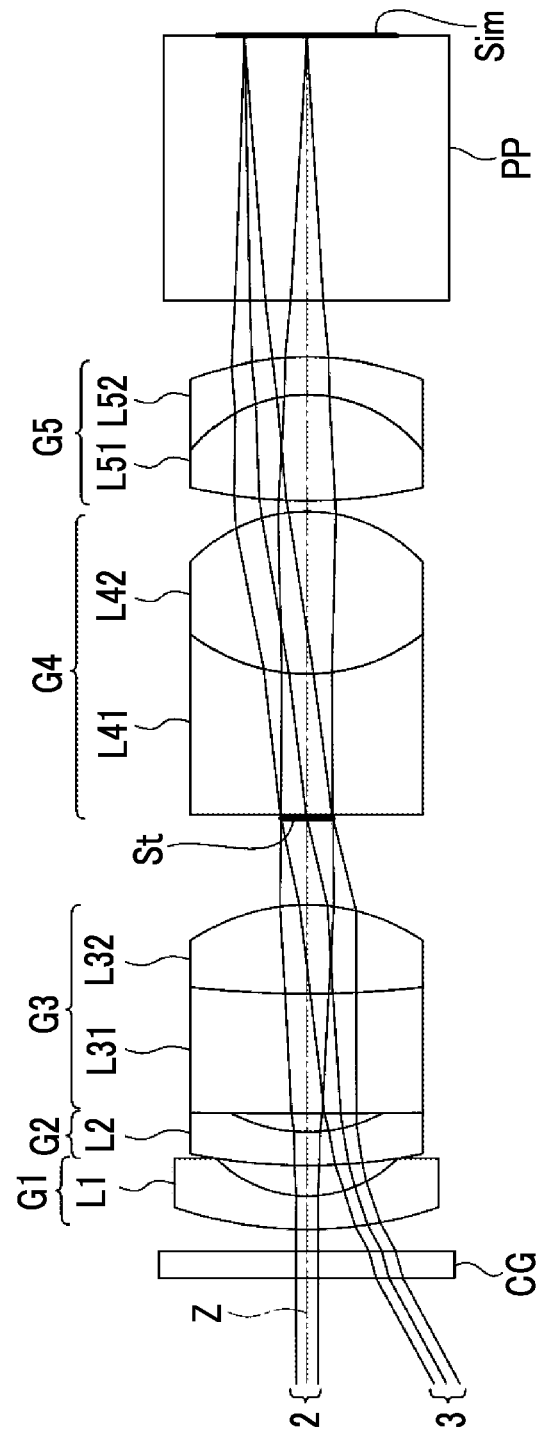
FIG. 5 is a cross-sectional view showing the configuration of an objective lens for an endoscope of Example 4 of the disclosure and luminous flux.

A cross-sectional view showing the configuration of an objective lens for an endoscope of Example 4 and luminous flux is shown in FIG. 5. The objective lens for an endoscope of Example 4 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a negative lens L31 and a positive lens L32 arranged in this order from the object side and cemented to each other. The fourth lens group G4 consists of a cemented lens that includes a negative lens L41 and a positive lens L42 arranged in this order from the object side and cemented to each other. The fifth lens group G5 consists of a cemented lens that includes a positive lens L51 and a negative lens L52 arranged in this order from the object side and cemented to each other.

Figure 13:
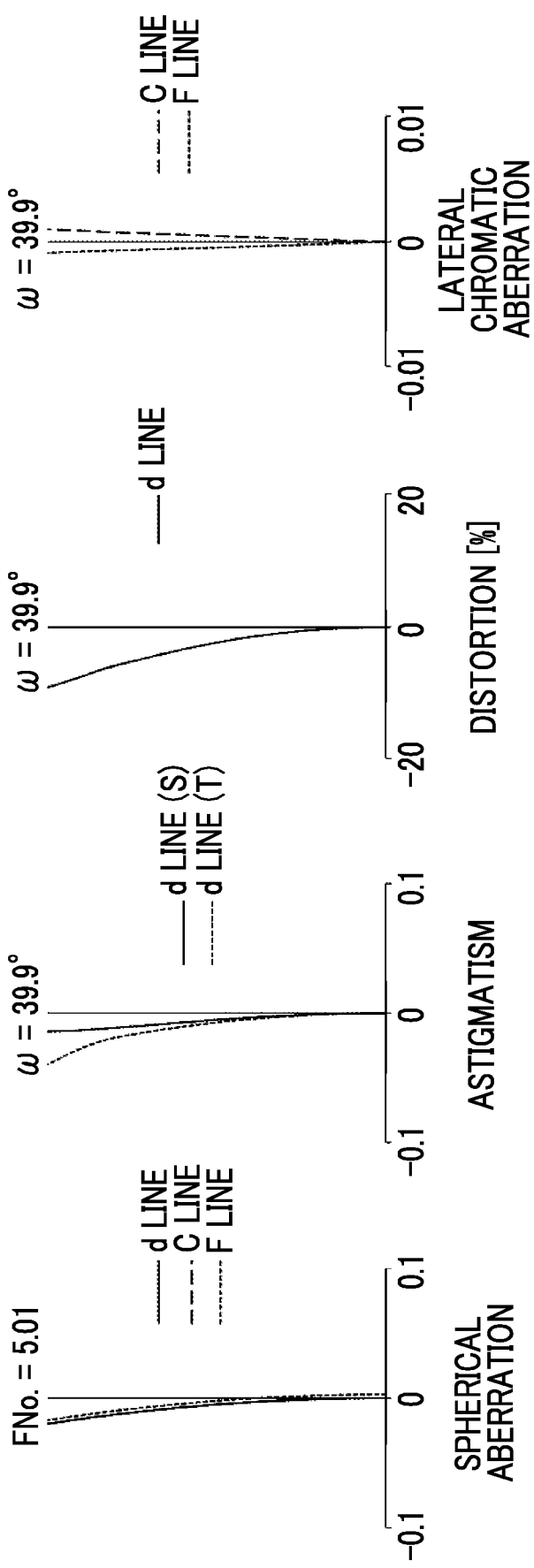
FIG. 13 is a diagram showing the respective aberrations of the objective lens for an endoscope of Example 4 of the disclosure.

The basic lens data of the objective lens for an endoscope of Example 4 are shown in Table 7, the specifications thereof are shown in Table 8, and a diagram showing the respective aberrations thereof is shown in FIG. 13. These data are data that are obtained in a case where a distance between an object and the surface of the cover glass CG close to the object side is set to 23.

TABLE 7

Example 4

| Sn | R | D | Nd | νd |
|---|---|---|---|---|
| 1 | ∞ | 0.2255 | 1.76800 | 71.70 |
| 2 | ∞ | 0.1804 | | |
| 3 | 3.5508 | 0.2797 | 2.00100 | 29.13 |
| 4 | 1.1277 | 0.2526 | | |
| 5 | 5.1061 | 0.2797 | 2.00100 | 29.13 |
| 6 | 1.4380 | 0.1534 | | |
| 7 | 90.2148 | 0.9924 | 2.05090 | 26.94 |
| 8 | 9.0207 | 0.7397 | 2.00100 | 29.13 |
| 9 | −1.8043 | 0.7217 | | |
| 10(St) | ∞ | 0.0316 | | |
| 11 | ∞ | 1.1728 | 1.88299 | 40.78 |
| 12 | 1.6402 | 1.3532 | 1.51860 | 69.89 |
| 13 | −1.3753 | 0.0902 | | |
| 14 | 4.5254 | 0.8841 | 1.62041 | 60.29 |
| 15 | −1.2888 | 0.3067 | 2.00069 | 25.46 |
| 16 | −2.8152 | 0.4060 | | |
| 17 | ∞ | 2.3005 | 1.55920 | 53.92 |
| 18 | ∞ | 0.0000 | | |

TABLE 8

Example 4

| f | 1.00 |
|---|---|
| Bf | 1.85 |
| FNo. | 5.01 |
| 2ω(°) | 79.8 |

Example 5

Figure 6:
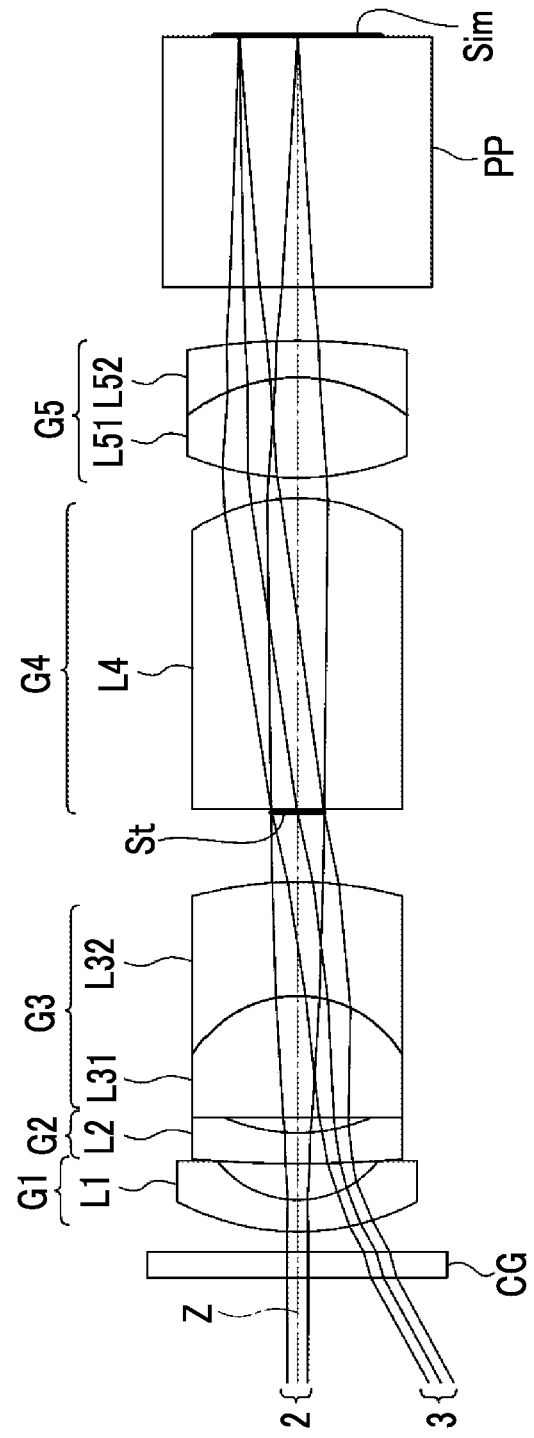
FIG. 6 is a cross-sectional view showing the configuration of an objective lens for an endoscope of Example 5 of the disclosure and luminous flux.

A cross-sectional view showing the configuration of an objective lens for an endoscope of Example 5 and luminous flux is shown in FIG. 6. The objective lens for an endoscope of Example 5 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a positive lens L4. The fifth lens group G5 consists of a cemented lens that includes a positive lens L51 and a negative lens L52 arranged in this order from the object side and cemented to each other.

Figure 14:
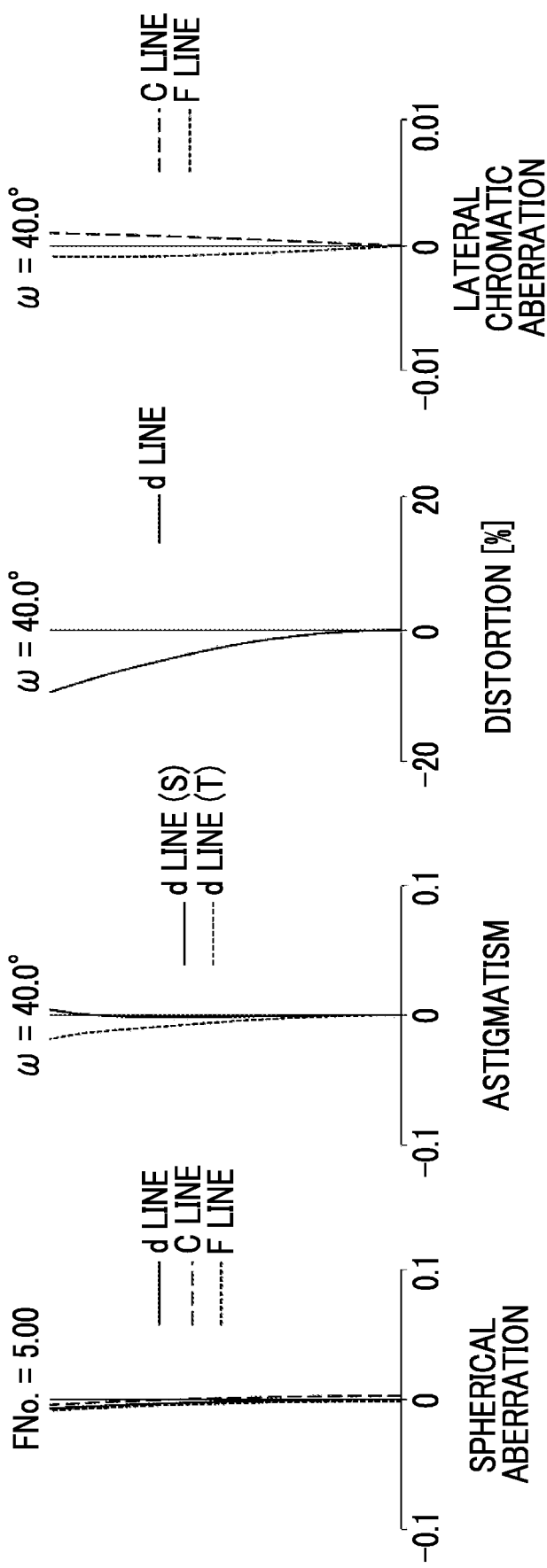
FIG. 14 is a diagram showing the respective aberrations of the objective lens for an endoscope of Example 5 of the disclosure.

The basic lens data of the objective lens for an endoscope of Example 5 are shown in Table 9, the specifications thereof are shown in Table 10, and a diagram showing the respective aberrations thereof is shown in FIG. 14. These data are data that are obtained in a case where a distance between an object and the surface of the cover glass CG close to the object side is set to 23.

TABLE 9

Example 5

| Sn | R | D | Nd | vd |
|---|---|---|---|---|
| 1 | ∞ | 0.2259 | 1.76800 | 71.70 |
| 2 | ∞ | 0.1807 | | |
| 3 | 2.3370 | 0.2802 | 2.00100 | 29.13 |
| 4 | 0.9534 | 0.3207 | | |
| 5 | 11.7999 | 0.2711 | 2.00100 | 29.13 |
| 6 | 1.7180 | 0.1356 | | |
| 7 | ∞ | 1.0754 | 1.90265 | 35.72 |
| 8 | −1.1297 | 1.0031 | 1.51860 | 69.89 |
| 9 | −3.6682 | 0.6145 | | |
| 10(St) | ∞ | 0.0316 | | |
| 11 | ∞ | 2.7383 | 1.43875 | 94.66 |
| 12 | −1.7180 | 0.1807 | | |
| 13 | 2.6551 | 0.8856 | 1.62041 | 60.29 |
| 14 | −1.6430 | 0.3253 | 2.00069 | 25.46 |
| 15 | −5.9447 | 0.4699 | | |
| 16 | ∞ | 2.2141 | 1.55920 | 53.92 |
| 17 | ∞ | 0.0000 | | |

TABLE 10

Example 5

| f | 1.00 |
|---|---|
| Bf | 1.86 |
| FNo. | 5.00 |
| 2ω(°) | 80.0 |

Example 6

Figure 7:
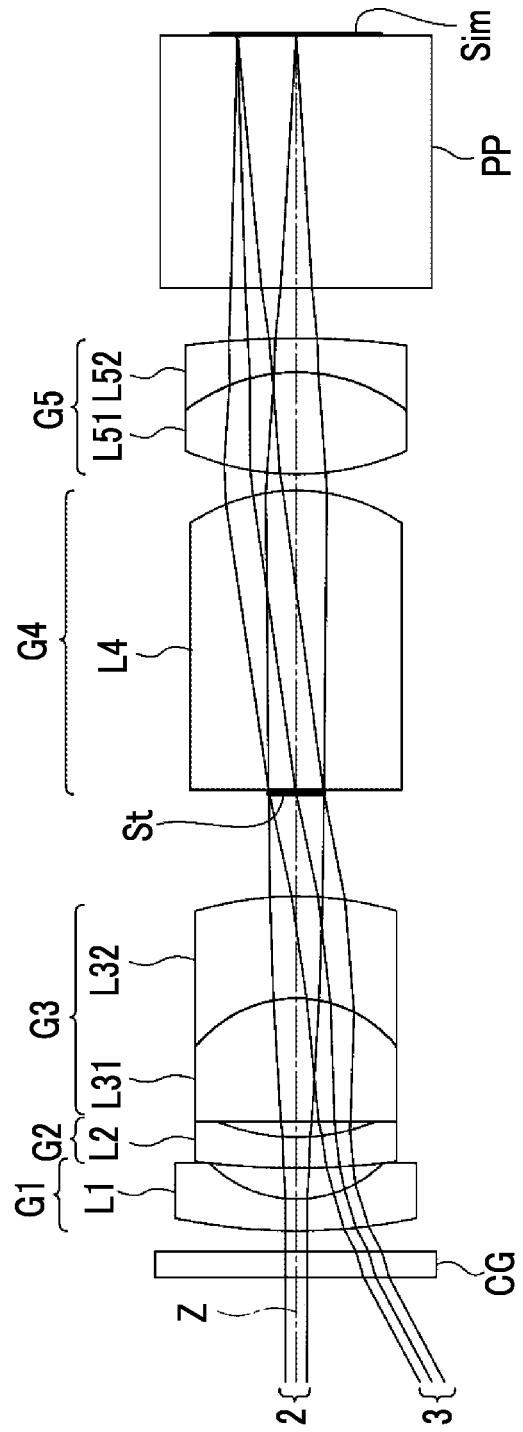
FIG. 7 is a cross-sectional view showing the configuration of an objective lens for an endoscope of Example 6 of the disclosure and luminous flux.

A cross-sectional view showing the configuration of an objective lens for an endoscope of Example 6 and luminous flux is shown in FIG. 7. The objective lens for an endoscope of Example 6 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a positive lens L4. The fifth lens group G5 consists of a cemented lens that includes a positive lens L51 and a negative lens L52 arranged in this order from the object side and cemented to each other.

Figure 15:
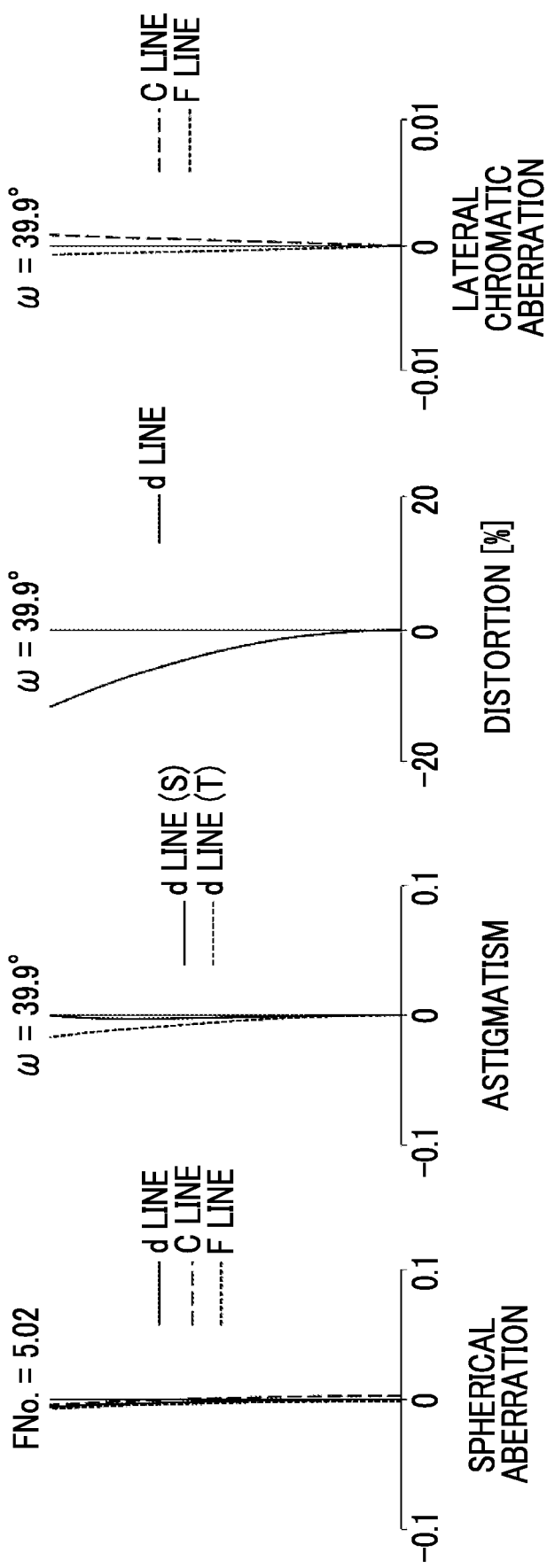
FIG. 15 is a diagram showing the respective aberrations of the objective lens for an endoscope of Example 6 of the disclosure.

The basic lens data of the objective lens for an endoscope of Example 6 are shown in Table 11, the specifications thereof are shown in Table 12, and a diagram showing the respective aberrations thereof is shown in FIG. 15. These data are data that are obtained in a case where a distance between an object and the surface of the cover glass CG close to the object side is set to 22.

TABLE 11

Example 6

| Sn | R | D | Nd | vd |
|---|---|---|---|---|
| 1 | ∞ | 0.2193 | 1.76800 | 71.70 |
| 2 | ∞ | 0.1754 | | |
| 3 | 5.0747 | 0.2719 | 2.00100 | 29.13 |
| 4 | 1.0965 | 0.2643 | | |
| 5 | 6.7932 | 0.2632 | 2.00100 | 29.13 |
| 6 | 1.8667 | 0.1316 | | |
| 7 | ∞ | 1.0527 | 1.90265 | 35.72 |
| 8 | −1.1439 | 0.8685 | 1.51860 | 69.89 |
| 9 | −3.1334 | 0.8772 | | |
| 10(St) | ∞ | 0.0307 | | |
| 11 | ∞ | 2.5439 | 1.43875 | 94.66 |
| 12 | −1.6676 | 0.1404 | | |
| 13 | 2.4422 | 0.8685 | 1.62041 | 60.29 |
| 14 | −1.5948 | 0.2895 | 2.00069 | 25.46 |
| 15 | −7.7774 | 0.4298 | | |
| 16 | ∞ | 2.1492 | 1.55920 | 53.92 |
| 17 | ∞ | 0.0000 | | |

TABLE 12

Example 6

| f | 1.00 |
|---|---|
| Bf | 1.77 |
| FNo. | 5.02 |
| 2ω(°) | 79.8 |

Example 7

Figure 8:
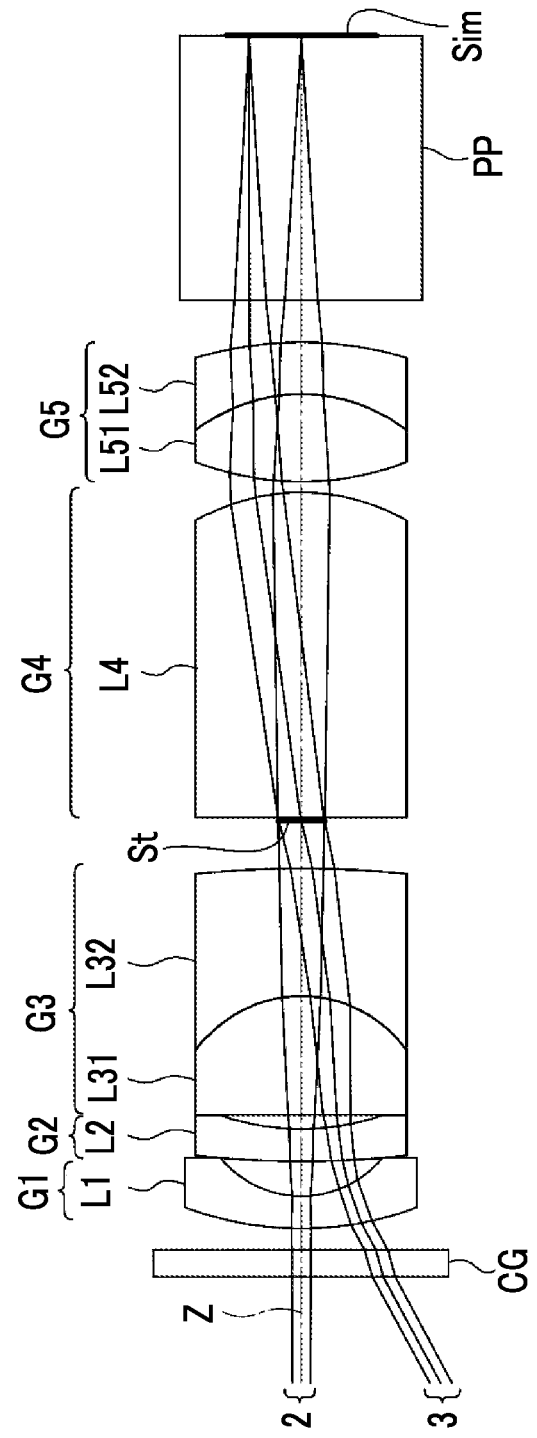
FIG. 8 is a cross-sectional view showing the configuration of an objective lens for an endoscope of Example 7 of the disclosure and luminous flux.

A cross-sectional view showing the configuration of an objective lens for an endoscope of Example 7 and luminous flux is shown in FIG. 8. The objective lens for an endoscope of Example 7 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a positive lens L4. The fifth lens group G5 consists of a cemented lens that includes a positive lens L51 and a negative lens L52 arranged in this order from the object side and cemented to each other.

Figure 16:
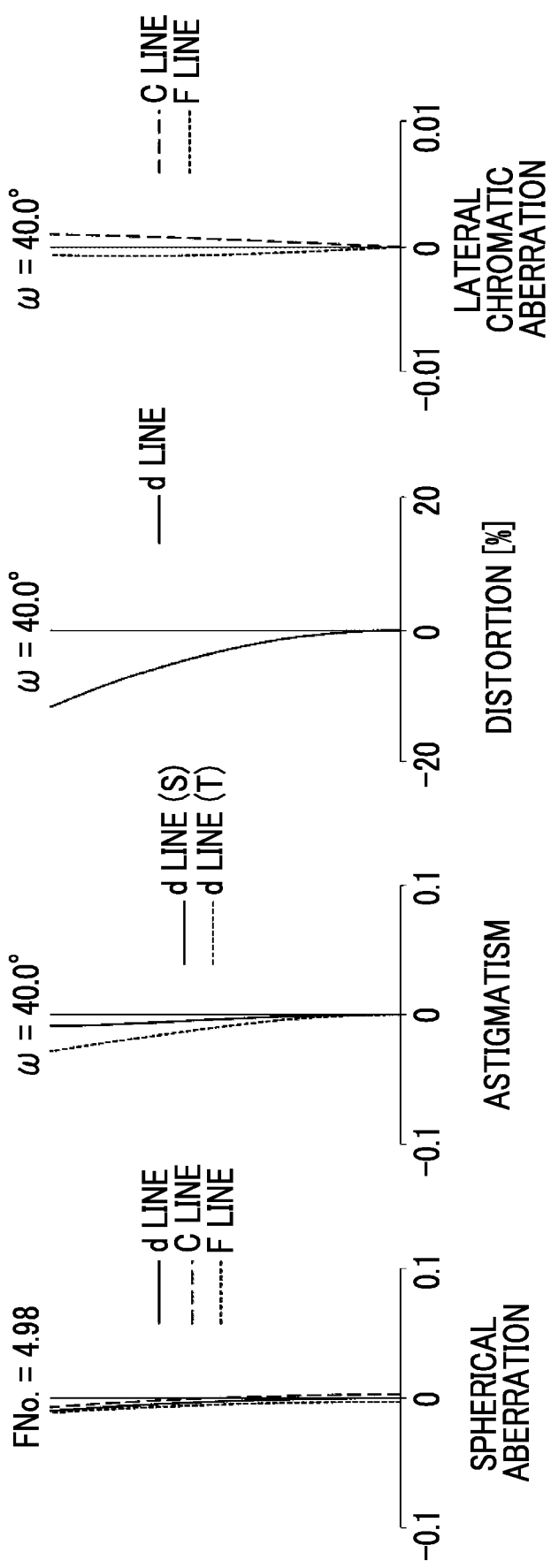
FIG. 16 is a diagram showing the respective aberrations of the objective lens for an endoscope of Example 7 of the disclosure.

The basic lens data of the objective lens for an endoscope of Example 7 are shown in Table 13, the specifications thereof are shown in Table 14, and a diagram showing the respective aberrations thereof is shown in FIG. 16. These data are data that are obtained in a case where a distance between an object and the surface of the cover glass CG close to the object side is set to 26.

TABLE 13

Example 7

| Sn | R | D | Nd | vd |
|---|---|---|---|---|
| 1 | ∞ | 0.2593 | 1.76800 | 71.70 |
| 2 | ∞ | 0.2074 | | |
| 3 | 3.3095 | 0.3111 | 2.00100 | 29.13 |
| 4 | 1.0600 | 0.3319 | | |
| 5 | 9.9078 | 0.3111 | 2.00100 | 29.13 |
| 6 | 2.5337 | 0.1348 | | |
| 7 | ∞ | 1.1409 | 2.00100 | 29.13 |
| 8 | −1.2964 | 1.2239 | 1.58144 | 40.75 |
| 9 | −10.4357 | 0.4563 | | |
| 10(St) | ∞ | 0.0363 | | |
| 11 | ∞ | 3.1114 | 1.58913 | 61.13 |
| 12 | −2.1199 | 0.1037 | | |
| 13 | 2.9662 | 0.8401 | 1.51860 | 69.89 |
| 14 | −1.7227 | 0.4978 | 1.92286 | 20.88 |
| 15 | −3.7047 | 0.4024 | | |
| 16 | ∞ | 2.5410 | 1.55920 | 53.92 |
| 17 | ∞ | 0.0000 | | |

TABLE 14

Example 7

| | |
|---|---|
| f | 1.00 |
| Bf | 2.00 |
| FNo. | 4.98 |
| 2ω(°) | 80.0 |

Example 8

Figure 9:
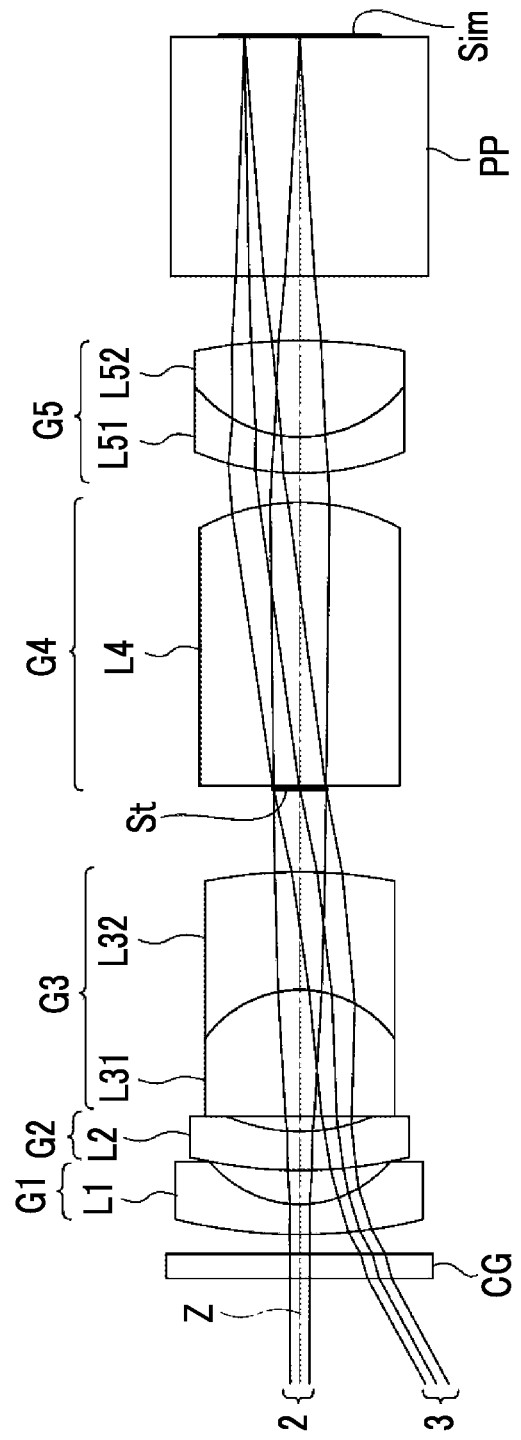
FIG. 9 is a cross-sectional view showing the configuration of an objective lens for an endoscope of Example 8 of the disclosure and luminous flux.

A cross-sectional view showing the configuration of an objective lens for an endoscope of Example 8 and luminous flux is shown in FIG. 9. The objective lens for an endoscope of Example 8 consists of a first lens group G1 having negative refractive power, a second lens group G2 having negative refractive power, a third lens group G3 having positive refractive power, an aperture stop St, a fourth lens group G4 having positive refractive power, and a fifth lens group G5 having positive refractive power that are arranged in this order from the object side toward the image side. The first lens group G1 consists of a negative lens L1. The second lens group G2 consists of a negative lens L2. The third lens group G3 consists of a cemented lens that includes a positive lens L31 and a negative lens L32 arranged in this order from the object side and cemented to each other. The fourth lens group G4 consists of a positive lens L4. The fifth lens group G5 consists of a cemented lens that includes a negative lens L51 and a positive lens L52 arranged in this order from the object side and cemented to each other.

Figure 17:
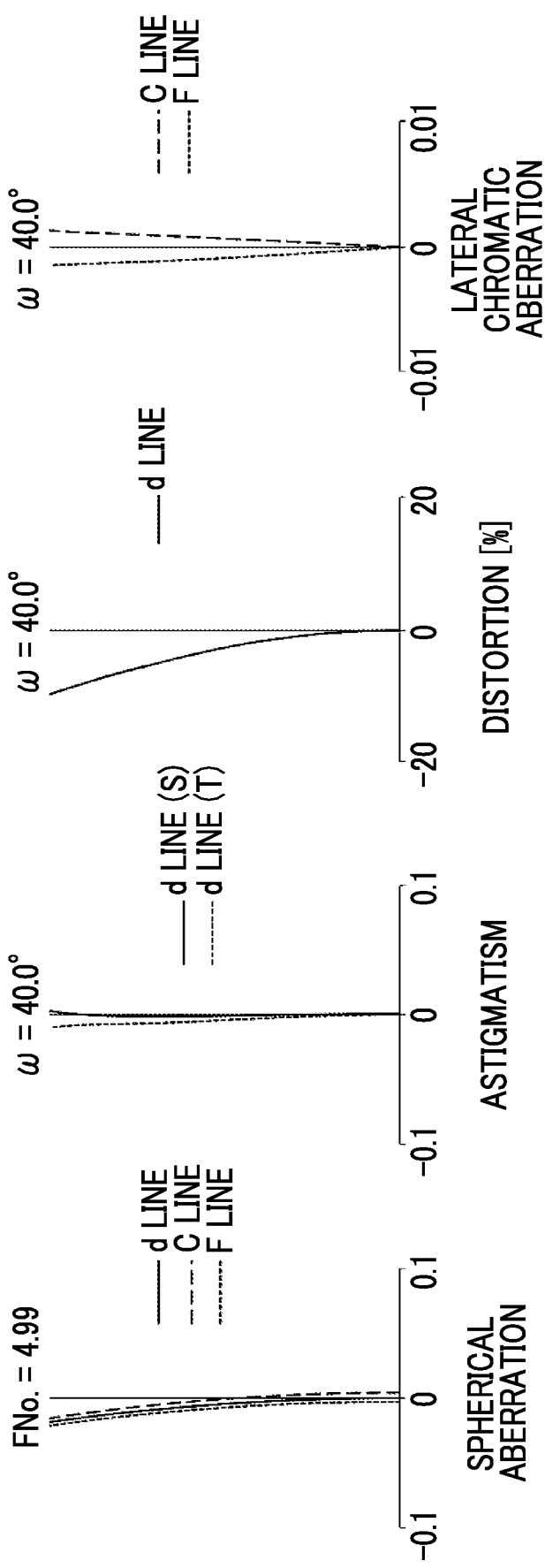
FIG. 17 is a diagram showing the respective aberrations of the objective lens for an endoscope of Example 8 of the disclosure.

The basic lens data of the objective lens for an endoscope of Example 8 are shown in Table 15, the specifications thereof are shown in Table 16, and a diagram showing the respective aberrations thereof is shown in FIG. 17. These data are data that are obtained in a case where a distance between an object and the surface of the cover glass CG close to the object side is set to 22.

TABLE 15

Example 8

| Sn | R | D | Nd | vd |
|---|---|---|---|---|
| 1 | ∞ | 0.2244 | 1.76500 | 10.00 |
| 2 | ∞ | 0.1795 | | |
| 3 | 4.9371 | 0.2783 | 2.00100 | 29.13 |
| 4 | 1.1220 | 0.3142 | | |
| 5 | 4.5071 | 0.3591 | 2.05090 | 26.94 |
| 6 | 1.7988 | 0.1356 | | |
| 7 | ∞ | 1.1670 | 1.90265 | 35.72 |
| 8 | −1.1220 | 1.0862 | 1.51860 | 69.89 |
| 9 | −4.7381 | 0.7609 | | |
| 10(St) | ∞ | 0.0314 | | |
| 11 | ∞ | 2.6032 | 1.43875 | 94.66 |
| 12 | −2.0122 | 0.2693 | | |
| 13 | 2.6006 | 0.3321 | 2.00069 | 25.46 |
| 14 | 1.2823 | 0.8887 | 1.62041 | 60.29 |
| 15 | −5.1132 | 0.5932 | | |
| 16 | ∞ | 2.1992 | 1.55920 | 53.92 |
| 17 | ∞ | 0.0000 | | |

TABLE 16

Example 8

| | |
|---|---|
| f | 1.00 |
| Bf | 1.97 |
| FNo. | 4.99 |
| 2ω(°) | 80.0 |

The values of Conditional expressions (1) to (7) corresponding to the objective lenses for an endoscope of Examples 1 to 8 are shown in Table 17. In Examples 1 to 8, a d line is used as a reference wavelength. Table 17 shows values with respect to a d line.

TABLE 17

| Expression number | | Example 1 | Example 2 | Example 3 | Example 4 |
|---|---|---|---|---|---|
| (1) | Σ\|(vai − vbi) × Dci/Rci\| | 136.20 | 192.02 | 127.81 | 117.18 |
| (2) | f12/f3 × (Rr1 + Rf1)/(Rr1 − Rf1) × (Rr2 + Rf2/(Rr2 − Rf2) | −1.15 | −1.02 | −1.47 | −1.66 |
| (3) | Rr3/f | −1.23 | −4.81 | −1.84 | −1.80 |
| (4) | Rr4/f | −1.43 | −1.88 | −1.43 | −1.37 |
| (5) | (Rr5 + Rf5)/(Rr5 − Rf5) | 0.36 | 0.52 | 0.03 | −0.23 |
| (6) | Df/Dr | 0.90 | 1.01 | 0.88 | 0.89 |
| (7) | \|f123/f45\| | 2.70 | 3.50 | 6.76 | 3.43 |
| Expression number | | Example 5 | Example 6 | Example 7 | Example 8 |
| (1) | Σ\|(vai − vbi) × Dci/Rci\| | 129.95 | 130.11 | 131.36 | 143.85 |
| (2) | f12/f3 × (Rr1 + Rf1)/(Rr1 − Rf1) × (Rr2 + Rf2/(Rr2 − Rf2) | −1.24 | −1.09 | −1.24 | −1.40 |
| (3) | Rr3/f | −3.66 | −3.13 | −10.42 | −4.73 |
| (4) | Rr4/f | −1.72 | −1.67 | −2.12 | −2.01 |
| (5) | (Rr5 + Rf5)/(Rr5 − Rf5) | 0.38 | 0.52 | 0.11 | 0.33 |
| (6) | Df/Dr | 0.90 | 0.97 | 0.86 | 1.00 |
| (7) | \|f123/f45\| | 2.83 | 3.78 | 1.94 | 2.84 |

As known from the above-mentioned data, the objective lenses for an endoscope of Examples 1 to 8 are formed to have a small size and aberrations including a chromatic aberration and distortion are corrected well. Accordingly, high optical performance is achieved.

Figure 18:
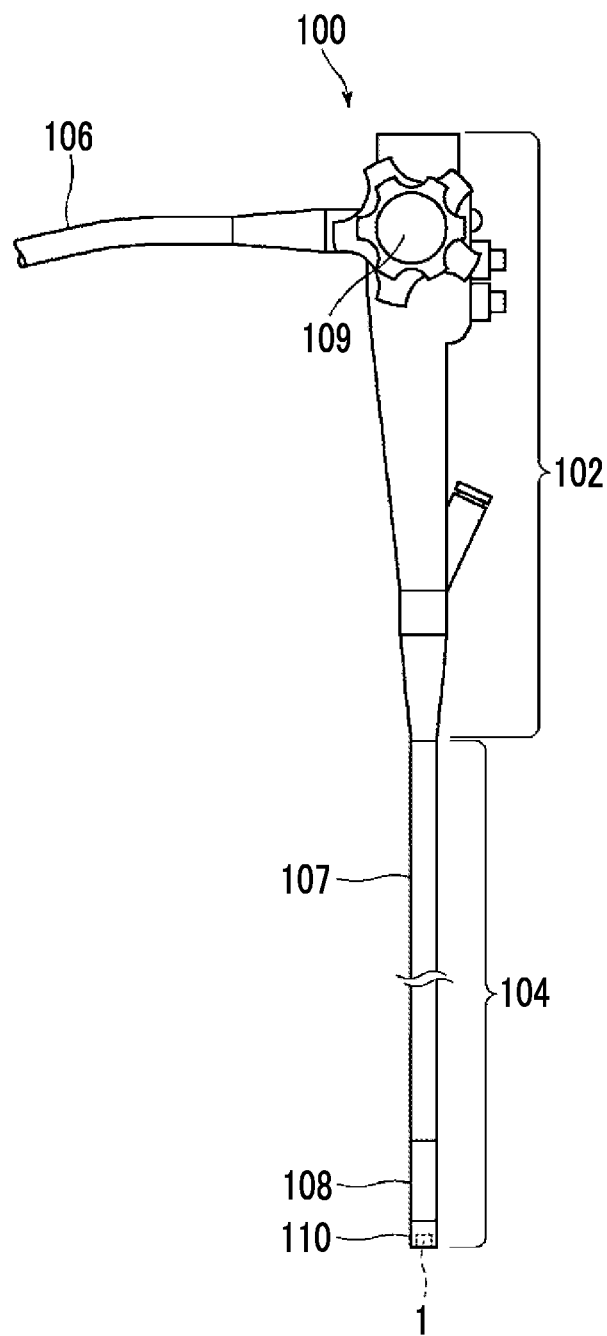
FIG. 18 is a diagram showing the schematic configuration of an endoscope according to an embodiment of the disclosure.

Next, an endoscope according to an embodiment of the disclosure will be described. A diagram showing the schematic configuration of the entire endoscope according to an embodiment of the disclosure is shown in FIG. 18. The endoscope 100 shown in FIG. 18 mainly comprises an operation part 102, an insertion part 104, and a universal cord 106 that is to be connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to face in a desired direction, and can be operated to be bent by the rotational movement of a bending operation knob 109 provided on the operation part 102. The objective lens 1 for an endoscope according to the embodiment of the disclosure is provided in the distal end of the distal end portion 110. The objective lens 1 for an endoscope is schematically shown in FIG. 18. Since the endoscope according to the embodiment of the disclosure comprises the objective lens for an endoscope according to the embodiment of the disclosure, the endoscope can acquire a good image.

A technique of the disclosure has been described above using the embodiments and the examples, but the technique of the disclosure may have various modifications without being limited to the embodiments and the examples. For example, the radius of curvature, the surface interval, the refractive index, the Abbe's number, and the like of each lens may have other values without being limited to values shown in the respective numerical examples.

What is claimed is:

1. An objective lens for an endoscope consisting of:
a first lens group that consists of a negative lens;
a second lens group that consists of a negative lens;
a third lens group that consists of a cemented lens formed by cementing two lenses;
an aperture stop;
a fourth lens group that consists of a single lens having positive refractive power or a cemented lens formed by cementing two lenses and having positive refractive power as a whole; and
a fifth lens group that consists of a cemented lens formed by cementing two lenses having refractive power having signs different from each other,
wherein the first lens group, the second lens group, the third lens group, the fourth lens group, and the fifth lens group are arranged in this order from an object side toward an image side,
in a case where a total number of the cemented lenses is denoted by k, a natural number of 1 to k is denoted by i, an Abbe's number of a lens, which forms an i-th cemented lens from the object side and is close to the object side, with respect to a d line is denoted by vai, an Abbe's number of a lens, which forms the i-th cemented lens from the object side and is close to the image side, with respect to a d line is denoted by vbi, a distance on an optical axis between the aperture stop and a cemented surface of the i-th cemented lens from the object side is denoted by Dci, and a radius of curvature of the cemented surface of the i-th cemented lens from the object side is denoted by Rci, Conditional expression (1) is satisfied $$100 < \sum_{i=1}^{k} \left| (vai - vbi) \times \frac{Dci}{Rci} \right|, \quad (1)$$

wherein in a case where a composite focal length of the first lens group, the second lens group, and the third lens group is denoted by f123 and a composite focal length of the fourth lens group and the fifth lens group is denoted by f45, Conditional expression (7) is satisfied, $$1.5 \leq |f123/f45| < 10 \quad (7).$$

2. The objective lens for an endoscope according to claim 1,
wherein in a case where a composite focal length of the first lens group and the second lens group is denoted by f12, a focal length of the third lens group is denoted by f3, a radius of curvature of a surface of the negative lens of the first lens group close to the image side is denoted by Rr1, a radius of curvature of a surface of the negative lens of the first lens group close to the object side is denoted by Rf1, a radius of curvature of a surface of the negative lens of the second lens group close to the image side is denoted by Rr2, and a radius of curvature of a surface of the negative lens of the second lens group close to the object side is denoted by Rf2, Conditional expression (2) is satisfied, $$-3 < \frac{f12}{f3} \times \frac{Rr1 + Rf1}{Rr1 - Rf1} \times \frac{Rr2 + Rf2}{Rr2 - Rf2} < -1 \quad (2).$$

3. The objective lens for an endoscope according to claim 1,
wherein in a case where a radius of curvature of a surface of the third lens group closest to the image side is denoted by Rr3 and a focal length of the objective lens for an endoscope is denoted by f, Conditional expression (3) is satisfied, $$-20 < Rr3/f < -0.5 \quad (3).$$

4. The objective lens for an endoscope according to claim 1,
wherein in a case where a radius of curvature of a surface of the fourth lens group closest to the image side is denoted by Rr4 and a focal length of the objective lens for an endoscope is denoted by f, Conditional expression (4) is satisfied, $$-2.5 < Rr4/f < -1 \quad (4).$$

5. The objective lens for an endoscope according to claim 1,
wherein in a case where a radius of curvature of a surface of the fifth lens group closest to the image side is denoted by Rr5 and a radius of curvature of a surface of the fifth lens group closest to the object side is denoted by Rf5, Conditional expression (5) is satisfied, $$-0.5 < (Rr5 + Rf5)/(Rr5 - Rf5) < 1 \quad (5).$$

6. The objective lens for an endoscope according to claim 1,
wherein in a case where a distance on the optical axis between the aperture stop and a lens surface closest to the object side is denoted by Df and a distance on the optical axis between the aperture stop and a lens surface closest to the image side is denoted by Dr, Conditional expression (6) is satisfied, $$0.5 < Df/Dr < 1.5 \qquad (6).$$

7. The objective lens for an endoscope according to claim 1, wherein Conditional expression (1-1) is satisfied, $$110 < \sum_{i=1}^{k} \left| (vai - vbi) \times \frac{Dci}{Rci} \right| < 200 \qquad (1\text{-}1).$$

8. The objective lens for an endoscope according to claim 2, wherein Conditional expression (2-1) is satisfied.

$$-1.8 < \frac{f12}{f3} \times \frac{Rr1 + Rf1}{Rr1 - Rf1} \times \frac{Rr2 + Rf2}{Rr2 - Rf2} < -1 \qquad (2\text{-}1).$$

9. The objective lens for an endoscope according to claim 3, wherein Conditional expression (3-1) is satisfied, $$-12 < Rr3/f < -1 \qquad (3\text{-}1).$$

10. The objective lens for an endoscope according to claim 4, wherein Conditional expression (4-1) is satisfied, $$-2.2 < Rr4/f < -1.2 \qquad (4\text{-}1).$$

11. The objective lens for an endoscope according to claim 5, wherein Conditional expression (5-1) is satisfied, $$-0.25 < (Rr5 + Rf5)/(Rr5 - Rf5) < 0.7 \qquad (5\text{-}1).$$

12. The objective lens for an endoscope according to claim 6, wherein Conditional expression (6-1) is satisfied, $$0.8 < Df/Dr < 1.2 \qquad (6\text{-}1).$$

13. The objective lens for an endoscope according to claim wherein Conditional expression (7-1) is satisfied, $$1.8 < |f123/f45| < 8 \qquad (7\text{-}1).$$

14. An endoscope comprising:
the objective lens for an endoscope according to claim 1.

15. An objective lens for an endoscope consisting of:
a first lens group that consists of a negative lens;
a second lens group that consists of a negative lens;
a third lens group that consists of a cemented lens formed by cementing two lenses;
an aperture stop;
a fourth lens group that consists of a single lens having positive refractive power or a cemented lens formed by cementing two lenses and having positive refractive power as a whole; and
a fifth lens group that consists of a cemented lens formed by cementing two lenses having refractive power having signs different from each other,
wherein the first lens group, the second lens group, the third lens group, the fourth lens group, and the fifth lens group are arranged in this order from an object side toward an image side,
in a case where a total number of the cemented lenses is denoted by k, a natural number of 1 to k is denoted by i, an Abbe's number of a lens, which forms an i-th cemented lens from the object side and is close to the object side, with respect to a d line is denoted by vai, an Abbe's number of a lens, which forms the i-th cemented lens from the object side and is close to the image side, with respect to a d line is denoted by vbi, a distance on an optical axis between the aperture stop and a cemented surface of the i-th cemented lens from the object side is denoted by Dci, and a radius of curvature of the cemented surface of the i-th cemented lens from the object side is denoted by Rci, Conditional expression (1) is satisfied $$100 < \sum_{i=1}^{k} \left| (vai - vbi) \times \frac{Dci}{Rci} \right|, \qquad (1)$$

wherein in a case where a distance on the optical axis between the aperture stop and a lens surface closest to the object side is denoted by Df and a distance on the optical axis between the aperture stop and a lens surface closest to the image side is denoted by Dr, wherein Conditional expression (6-1) is satisfied, $$0.8 < Df/Dr < 1.2 \qquad (6\text{-}1).$$

16. An endoscope comprising:
the objective lens for an endoscope according to claim 15.

* * * * *